(12) United States Patent
Lambert et al.

(10) Patent No.: US 6,448,226 B1
(45) Date of Patent: *Sep. 10, 2002

(54) BACILLUS THURINGIENSIS STRAINS AND THEIR INSECTICIDAL PROTEINS

(75) Inventors: Bart Lambert, Beernum; Stefan Jansens, Ghent; Katrien Van Audenhove, Ghent; Marnix Peferoen, Ghent; Jeroen Van Rie, Eeklo; Roel Van Aarssen, Ghent, all of (BE)

(73) Assignee: Aventis CropScience N.V., Ghent (BE)

( * ) Notice: Subject to any disclaimer, the term of this patent is extended or adjusted under 35 U.S.C. 154(b) by 0 days.

This patent is subject to a terminal disclaimer.

(21) Appl. No.: 09/471,177

(22) Filed: Dec. 23, 1999

Related U.S. Application Data

(62) Division of application No. 09/019,809, filed on Feb. 6, 1998, now Pat. No. 6,143,550, which is a division of application No. 08/532,547, filed as application No. PCT/EP94/00553 on Feb. 25, 1994, now Pat. No. 5,861,543.

(30) Foreign Application Priority Data

| Apr. 9, 1993 | (GB) | ............................................. 93400949 |
| Jul. 12, 1993 | (EP) | ................................. PCT/EP93/01820 |

(51) Int. Cl.$^7$ ........................ A01N 37/18; C07K 14/325
(52) U.S. Cl. .......................... 514/12; 514/2; 530/350; 530/825; 424/832
(58) Field of Search .................................. 530/350, 825; 514/2, 12; 424/832

(56) References Cited

U.S. PATENT DOCUMENTS 5,763,245 A * 6/1998 Greenplate et al. ....... 435/172.3
5,885,571 A * 3/1999 Lambert et al. ....... 434/94.461

FOREIGN PATENT DOCUMENTS

| EP | 0358557 | 3/1990 |
| EP | 0408403 | 1/1991 |
| EP | 0440581 | 1/1991 |
| EP | 0498537 | 1/1992 |
| WO | 90/06999 | 6/1990 |
| WO | 93/04587 | 3/1993 |

OTHER PUBLICATIONS

Gleave et al., J. General Microbiology, 138, 55–62 (1992).

Smulevitch et al., FEBS LETTERS, 293, 25–37 (1991).

Vaeck et al., Nature, 328, 33–37 (1987).

Hofte et al., Microbiological Reviews, 53, 242–255 (1989).

Ge et al., J. Biological Chemistry, 266, 17954–17958 (1991).

Reynaerts et al., Med. Fac. Landbouww. Rijksuniv. Gent., 51/3b, 1173–1178 (1986).

* cited by examiner

*Primary Examiner*—Gabrielle Bugaisky
(74) *Attorney, Agent, or Firm*—Birch, Stewart, Kolasch & Birch, LLP

(57) ABSTRACT

The present invention relates to transformed plants and plant cells comprising DNA molecules encoding *Bacillus thuringiensis* proteins with insecticidal activity. The invention relates more particularly to transformed plants and plant cells comprising DNA molecules encoding the protease resistant toxins BTS02618Aa or BTS02618Ab, as well as to methods of rendering plants or plant cells resistant to insects using these DNA molecules.

5 Claims, 1 Drawing Sheet

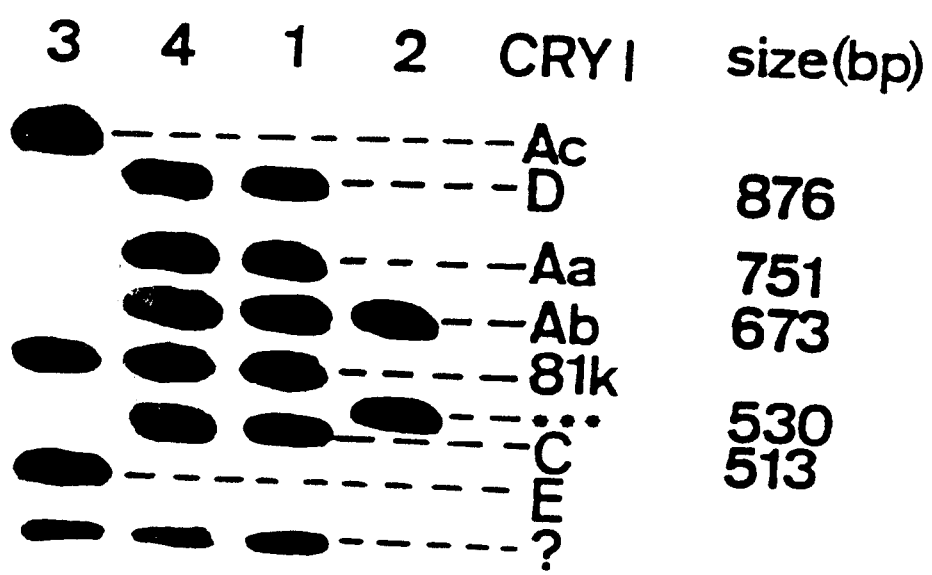

SEQUENCE LISTING (1) GENERAL INFORMATION:

(iii) NUMBER OF SEQUENCES: 9

(2) INFORMATION FOR SEQ ID NO: 1:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 1..19
        (D) OTHER INFORMATION: /function= "for isolating bTS02618A
            gene from its containing strain"
            /note= "the probe is a part of the coding DNA
            strand of the cryIG gene (Smulevitch et al. (1991)"

(xi) SEQUENCE DESCRIPTION: SEQ ID NO: 1:

TTCTGTACTA TTGATTGTA                                                    19

(2) INFORMATION FOR SEQ ID NO: 2:

(i) SEQUENCE CHARACTERISTICS:
        (A) LENGTH: 1561 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Bacillus thuringiensis
        (B) STRAIN: BTS02618A (ix) FEATURE:
        (A) NAME/KEY: misc_feature
        (B) LOCATION: 1..1561
        (D) OTHER INFORMATION: /note= "contains the translation
            initiation codon of the bTS02618A gene"

(xi) SEQUENCE DESCRIPTION: SEQ ID NO: 2:

```
AAAAAGAAAT AGGAATAAAT ACTATCCATT TTTTCAAGAA ATATTTTTTT ATTAGAAAGG     60

AATCTTTCTT ACACGGGAAA ATCCTAAGAT TGAGAGTAAA GATATATATA TATAAATACA    120

ATAAAGAGTT TGTCAGGATT TTTGAAAGAT ATGATATGAA CATGCACTAG ATTTATAGTA    180

TAGGAGGAAA AAGTATGAAT CGAAATAATC AAAATGAATA TGAAATTATT GATGCCCCCC    240

ATTGTGGGTG TCCATCAGAT GACGATGTGA GGTATCCTTT GGCAAGTGAC CCAAATGCAG    300

CGTTACAAAA TATGAACTAT AAAGATTACT TACAAATGAC AGATGAGGAC TACACTGATT    360

CTTATATAAA TCCTAGTTTA TCTATTAGTG GTAGAGATGC AGTTCAGACT GCGCTTACTG    420

TTGTTGGGAG AATACTCGGG GCTTTAGGTG TTCCGTTTTC TGGACAAATA GTGAGTTTTT    480

ATCAATTCCT TTTAAATACA CTGTGGCCAG TTAATGATAC AGCTATATGG GAAGCTTTCA    540

TGCGACAGGT GGAGGAACTT GTCAATCAAC AAATAACAGA ATTTGCAAGA AATCAGGCAC    600

TTGCAAGATT GCAAGGATTA GGAGACTCTT TTAATGTATA TCAACGTTCC CTTCAAAATT    660

GGTTGGCTGA TCGAAATGAT ACACGAAATT TAAGTGTTGT TCGTGCTNAA TTTATAGCTT    720

TGGAACTAAC CGCTAAGTAC ACTAATTACT GTGAAACTTG GTATAATACA GGTTTAGATC    960

GTTTAAGAGG AACAAATACT GAAAGTTGGT TAAGATATCA TCAATTCCGT AGAGAAATGA   1020

CTTTAGTGGT ATTAGATGTT GTGGCGCTAT TTCCATATTA TGATGTACGA CTTTATCCAA   1080

CGGGATCAAA CCCACAGCTT ACACGTGAGG TATATACAGA TCCGATTGTA TTTAATCCAC   1140

CAGCTAATGT TGGACTTTGC CGACGTTGGG GTACTAATCC CTATAATACT TTTTCTGAGC   1200

TCGAAAATGC CTTCATTCGC CCACCACATC TTTTTGATAG GCTGAATAGC TTAACAATCA   1260
```

-continued

```
GCAGTAATCG ATTTCCAGTT TCATCTAATT TTATGGATTA TTGGTCAGGA CATACGTTAC   1320

GCCGTAGTTA TCTGAACGAT TCAGCAGTAC AAGAAGATAG TTATGGCCTA ATTACAACCA   1380

CAAGAGCAAC AATTAATCCC GGAGTTGATG GAACAAACCG CATAGAGTCA ACGGCAGTAG   1440

ATTTTCGTTC TGCATTGATA GGTATATATG GCGTGAATAG AGCTTCTTTT GTCCCAGGAG   1500

GCTTGTTTAA TGGTACGACT TCTCCTGCTA ATGGAGGATG TAGAGATCTC TATGATACAA   1560

A                                                                   1561
```

(2) INFORMATION FOR SEQ ID NO: 3:

(i) SEQUENCE CHARACTERISTICS:
(A) LENGTH: 1554 base pairs
(B) TYPE: nucleic acid
(C) STRANDEDNESS: double
(D) TOPOLOGY: linear (ii) MOLECULE TYPE: DNA (genomic)

(vi) ORIGINAL SOURCE:
(A) ORGANISM: Bacillus thuringiensis
(B) STRAIN: BTS02618A (ix) FEATURE:
(A) NAME/KEY: misc_feature
(B) LOCATION: 1146..1148
(D) OTHER INFORMATION: /function= "Presumed translational stop codon of bTS02618A gene"

(xi) SEQUENCE DESCRIPTION: SEQ ID NO: 3:

```
AAAATTATCC AACATACATT TATCAAAAAG TAGATGCATC GGTGTTAAAG CCTTATACAC     60

GCTATAGACT AGATGGATTT GTGAAGNGTA GTCAAGATTT AGAAATTGAT CTCATCCACC    120

ATCATAAAGT CCATCTTGTA AAAAATGTAC CAGATAATTT AGTATCTGAT ACTTACTCAG    180

ATGGTTCTTG CAGCGGAATC AACCGTTGTG ATGAACAGCA TCAGGTAGAT ATGCAGCTAG    240

ATGCGGAGCA TCATCCAATG GATTGCTGTG AAGCGGCTCA AACACATGAG TTTTCTTCCT    300

ATATTAATAC AGGGGATCTA AATGCAAGTG TAGATCAGGG CATTTGGGTT GTATTAAAAG    360

TTCGAACAAC AGATGGGTAT GCGACGTTAG GAAATCTTGA ATTGGTAGAG GTTGGGCCAT    420

TATCGGGTGA ATCTCTAGAA CGGGAACAAA GAGATAATGC GAAATGGAAT GCAGAGCTAG    480

GAAGAAAACG TGCAGAAATA GATCGTGTGT ATTTAGCTGC GAAACAAGCA ATTAATCATC    540

TGTTTGTAGA CTATCAAGAT CAACAATTAA ATCCAGAAAT TGGGCTAGCA GAAATTAATG    600

AAGCTTCAAA TCTTGTAGAG TCAATTTCGG GTGTATATAG TGATACACTA TTACAGATTC    660

CTGGGATTAA CTACGAAATT TACACAGAGT TATCCGATCG CTTACAACAA GCATCGTATC    720

TGTATACGTC TAGAAATGCG GTGCAAAATG GAGACTTTAA CAGTGGTCTA GATAGTTGGA    780

ATACAACTAT GGATGCATCG GTTCAGCAAG ATGGCAATAT GCATTTCTTA GTTCTTTCGC    840

ATTGGGATGC ACAAGTTTCC CAACAATTGA GAGTAAATCC GAATTGTAAG TATGTCTTAC    900

GTGTGACAGC AAGAAAAGTA GGAGGCGGAG ATGGATACGT CACAATCCGA GATGGCGCTC    960

ATCACCAAGA AACTCTTACA TTTAATGCAT GTGACTACGA TGTAAATGGT ACGTATGTCA   1020

ATGACAATTC GTATATAACA GAAGAAGTGG TATTCTACCC AGAGACAAAA CATATGTGGG   1080

TAGAGGTGAG TGAATCCGAA GGTTCATTCT ATATAGACAG TATTGAGTTT ATTGAAACAC   1140

AAGAGTAGAA GAGGGGGATC CTAACGTATA GCAACTATGA GAGGATACTC CGTACAAACA   1200

AAGATTAAAA AAAGGTAAAA TGAATAGAAC CCCCTACTGG TAGAAGGACC GATAGGGGGT   1260

TCTTACATGA AAAAATGTAG CTGTTTACTA AGGTGTATAA AAAACAGCAT ATCTGATAGA   1320
```

-continued

```
AAAAAGTGAG TACCTTATAA AGAAAGAATT CCATTCACAG TTTCGGTATC ATATAAATAA    1380

TGATAGGGGT ATCCTTCTTA TTTACATTAT TTTTCGCAAT TATCTCGACG TTCTTCTTTC    1440

CGCTCACAAT GATGATGATC ATGACAACAA TCGCGTCCAT AGCGAACTCT TTCGATATTA    1500

ATAATATCTA AACTCGTGTA GCAGTCATTT CCATTTTTTT TGATCCAGTA AATA          1554
```

(2) INFORMATION FOR SEQ ID NO: 4:

(i) SEQUENCE CHARACTERISTICS:
        (A) LENGTH: 4344 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 668..4141

(ix) FEATURE:
        (A) NAME/KEY: misc_feature
        (B) LOCATION: 1..4344
        (D) OTHER INFORMATION: /note= "encompasses entire sequence
            of SEQ ID NO (SID) 2: from nt position 474 to 2034
            in SID 4"

(ix) FEATURE:
        (A) NAME/KEY: misc_feature
        (B) LOCATION: 1..4344
        (D) OTHER INFORMATION: /note= "also encompasses part of
            the sequence of SID 3: from nt position 2994 to
            4344 in SID 4"

(ix) FEATURE:
        (A) NAME/KEY: misc_feature
        (B) LOCATION: 1..4344
        (D) OTHER INFORMATION: /note= "SID 3 shows additional
            nucleotides, located 3' from the sequence shown in
            SID 4 (1352-1554 in SID 4)"

(xi) SEQUENCE DESCRIPTION: SEQ ID NO: 4:

```
GAATTCGAGC TCGGTACCTT TTCAGTGTAT CGTTTCCCTT CCATCAGGTT TTCAAATTGA     60

AAGCCGAAT GATTTGAAAC TTGTTTACGA TGTAAGTCAT TTGTCTATGA CGAAAGATAC     120

GTGTAAAAAA CGTATTGAGA TTGATGAATG TGGACAAGTA GAAATTGACT TACAAGTATT    180

AAAGATTAAG GGTGTCCTTT CTTTTATCGG AAATTTCTCT ATTGAACCTA TTCTGTGTGA    240

AAACATGTAT ACAACGGTTG ATAGAGATCC GTCTATTTCC TTAAGTTTCC AAGATACGGT    300

ATATGTGGAC CATATTTTAA AATATAGCGT CCAACAACTA CCATATTATG TAATTGATGG    360

TGATCATATT CAAGTACGTG ATTTACAAAT CAAACTGATG AAAGAGAATC CGCAATCTGC    420

TCAAGTATCA GGTTTGTTTT GTTTTGTATA TGAGTAAGAA CCGAAGGTTT GTAAAAAGA     480

AATAGGAATA AATACTATCC ATTTTTTCAA GAAATATTTT TTTATTAGAA AGGAATCTTT    540

CTTACACGGG AAAATCCTAA GATTGAGAGT AAAGATATAT ATATATAAAT ACAATAAAGA    600

GTTTGTCAGG ATTTTTGAAA GATATGATAT GAACATGCAC TAGATTTATA GTATAGGAGG    660
```

```
AAAAAGT ATG AAT CGA AAT AAT CAA AAT GAA TAT GAA ATT ATT GAT GCC     709
        Met Asn Arg Asn Asn Gln Asn Glu Tyr Glu Ile Ile Asp Ala
          1               5                  10

CCC CAT TGT GGG TGT CCA TCA GAT GAC GAT GTG AGG TAT CCT TTG GCA     757
Pro His Cys Gly Cys Pro Ser Asp Asp Asp Val Arg Tyr Pro Leu Ala
 15              20                  25                  30

AGT GAC CCA AAT GCA GCG TTA CAA AAT ATG AAC TAT AAA GAT TAC TTA     805
Ser Asp Pro Asn Ala Ala Leu Gln Asn Met Asn Tyr Lys Asp Tyr Leu
             35                  40                  45
```

```
CAA ATG ACA GAT GAG GAC TAC ACT GAT TCT TAT ATA AAT CCT AGT TTA      853
Gln Met Thr Asp Glu Asp Tyr Thr Asp Ser Tyr Ile Asn Pro Ser Leu
            50                  55                  60

TCT ATT AGT GGT AGA GAT GCA GTT CAG ACT GCG CTT ACT GTT GTT GGG      901
Ser Ile Ser Gly Arg Asp Ala Val Gln Thr Ala Leu Thr Val Val Gly
            65                  70                  75

AGA ATA CTC GGG GCT TTA GGT GTT CCG TTT TCT GGA CAA ATA GTG AGT      949
Arg Ile Leu Gly Ala Leu Gly Val Pro Phe Ser Gly Gln Ile Val Ser
            80                  85                  90

TTT TAT CAA TTC CTT TTA AAT ACA CTG TGG CCA GTT AAT GAT ACA GCT      997
Phe Tyr Gln Phe Leu Leu Asn Thr Leu Trp Pro Val Asn Asp Thr Ala
 95                 100                 105                 110

ATA TGG GAA GCT TTC ATG CGA CAG GTG GAG GAA CTT GTC AAT CAA CAA     1045
Ile Trp Glu Ala Phe Met Arg Gln Val Glu Glu Leu Val Asn Gln Gln
                115                 120                 125

ATA ACA GAA TTT GCA AGA AAT CAG GCA CTT GCA AGA TTG CAA GGA TTA     1093
Ile Thr Glu Phe Ala Arg Asn Gln Ala Leu Ala Arg Leu Gln Gly Leu
                130                 135                 140

GGA GAC TCT TTT AAT GTA TAT CAA CGT TCC CTT CAA AAT TGG TTG GCT     1141
Gly Asp Ser Phe Asn Val Tyr Gln Arg Ser Leu Gln Asn Trp Leu Ala
                145                 150                 155

GAT CGA AAT GAT ACA CGA AAT TTA AGT GTT GTT CGT GCT CAA TTT ATA     1189
Asp Arg Asn Asp Thr Arg Asn Leu Ser Val Val Arg Ala Gln Phe Ile
            160                 165                 170

GCT TTA GAC CTT GAT TTT GTT AAT GCT ATT CCA TTG TTT GCA GTA AAT     1237
Ala Leu Asp Leu Asp Phe Val Asn Ala Ile Pro Leu Phe Ala Val Asn
175                 180                 185                 190

GGA CAG CAG GTT CCA TTA CTG TCA GTA TAT GCA CAA GCT GTG AAT TTA     1285
Gly Gln Gln Val Pro Leu Leu Ser Val Tyr Ala Gln Ala Val Asn Leu
                195                 200                 205

CAT TTG TTA TTA TTA AAA GAT GCA TCT CTT TTT GGA GAA GGA TGG GGA     1333
His Leu Leu Leu Leu Lys Asp Ala Ser Leu Phe Gly Glu Gly Trp Gly
                210                 215                 220

TTC ACA CAG GGG GAA ATT TCC ACA TAT TAT GAC CGT CAA TTG GAA CTA     1381
Phe Thr Gln Gly Glu Ile Ser Thr Tyr Tyr Asp Arg Gln Leu Glu Leu
                225                 230                 235

ACC GCT AAG TAC ACT AAT TAC TGT GAA ACT TGG TAT AAT ACA GGT TTA     1429
Thr Ala Lys Tyr Thr Asn Tyr Cys Glu Thr Trp Tyr Asn Thr Gly Leu
            240                 245                 250

GAT CGT TTA AGA GGA ACA AAT ACT GAA AGT TGG TTA AGA TAT CAT CAA     1477
Asp Arg Leu Arg Gly Thr Asn Thr Glu Ser Trp Leu Arg Tyr His Gln
255                 260                 265                 270

TTC CGT AGA GAA ATG ACT TTA GTG GTA TTA GAT GTT GTG GCG CTA TTT     1525
Phe Arg Arg Glu Met Thr Leu Val Val Leu Asp Val Val Ala Leu Phe
                275                 280                 285

CCA TAT TAT GAT GTA CGA CTT TAT CCA ACG GGA TCA AAC CCA CAG CTT     1573
Pro Tyr Tyr Asp Val Arg Leu Tyr Pro Thr Gly Ser Asn Pro Gln Leu
                290                 295                 300

ACA CGT GAG GTA TAT ACA GAT CCG ATT GTA TTT AAT CCA CCA GCT AAT     1621
Thr Arg Glu Val Tyr Thr Asp Pro Ile Val Phe Asn Pro Pro Ala Asn
                305                 310                 315

GTT GGA CTT TGC CGA CGT TGG GGT ACT AAT CCC TAT AAT ACT TTT TCT     1669
Val Gly Leu Cys Arg Arg Trp Gly Thr Asn Pro Tyr Asn Thr Phe Ser
            320                 325                 330

GAG CTC GAA AAT GCC TTC ATT CGC CCA CCA CAT CTT TTT GAT AGG CTG     1717
Glu Leu Glu Asn Ala Phe Ile Arg Pro Pro His Leu Phe Asp Arg Leu
335                 340                 345                 350

AAT AGC TTA ACA ATC AGC AGT AAT CGA TTT CCA GTT TCA TCT AAT TTT     1765
Asn Ser Leu Thr Ile Ser Ser Asn Arg Phe Pro Val Ser Ser Asn Phe
```

```
                      355                  360                       365
ATG GAT TAT TGG TCA GGA CAT ACG TTA CGC CGT AGT TAT CTG AAC GAT       1813
Met Asp Tyr Trp Ser Gly His Thr Leu Arg Arg Ser Tyr Leu Asn Asp
                370                 375                 380

TCA GCA GTA CAA GAA GAT AGT TAT GGC CTA ATT ACA ACC ACA AGA GCA       1861
Ser Ala Val Gln Glu Asp Ser Tyr Gly Leu Ile Thr Thr Thr Arg Ala
            385                 390                 395

ACA ATT AAT CCC GGA GTT GAT GGA ACA AAC CGC ATA GAG TCA ACG GCA       1909
Thr Ile Asn Pro Gly Val Asp Gly Thr Asn Arg Ile Glu Ser Thr Ala
        400                 405                 410

GTA GAT TTT CGT TCT GCA TTG ATA GGT ATA TAT GGC GTG AAT AGA GCT       1957
Val Asp Phe Arg Ser Ala Leu Ile Gly Ile Tyr Gly Val Asn Arg Ala
415                 420                 425                 430

TCT TTT GTC CCA GGA GGC TTG TTT AAT GGT ACG ACT TCT CCT GCT AAT       2005
Ser Phe Val Pro Gly Gly Leu Phe Asn Gly Thr Thr Ser Pro Ala Asn
                435                 440                 445

GGA GGA TGT AGA GAT CTC TAT GAT ACA AAT GAT GAA TTA CCA CCA GAT       2053
Gly Gly Cys Arg Asp Leu Tyr Asp Thr Asn Asp Glu Leu Pro Pro Asp
            450                 455                 460

GAA AGT ACC GGA AGT TCA ACC CAT AGA CTA TCT CAT GTT ACC TTT TTT       2101
Glu Ser Thr Gly Ser Ser Thr His Arg Leu Ser His Val Thr Phe Phe
        465                 470                 475

AGC TTT CAA ACT AAT CAG GCT GGA TCT ATA GCT AAT GCA GGA AGT GTA       2149
Ser Phe Gln Thr Asn Gln Ala Gly Ser Ile Ala Asn Ala Gly Ser Val
    480                 485                 490

CCT ACT TAT GTT TGG ACC CGT CGT GAT GTG GAC CTT AAT AAT ACG ATT       2197
Pro Thr Tyr Val Trp Thr Arg Arg Asp Val Asp Leu Asn Asn Thr Ile
495                 500                 505                 510

ACC CCA AAT AGA ATT ACA CAA TTA CCA TTG GTA AAG GCA TCT GCA CCT       2245
Thr Pro Asn Arg Ile Thr Gln Leu Pro Leu Val Lys Ala Ser Ala Pro
                515                 520                 525

GTT TCG GGT ACT ACG GTC TTA AAA GGT CCA GGA TTT ACA GGA GGG GGT       2293
Val Ser Gly Thr Thr Val Leu Lys Gly Pro Gly Phe Thr Gly Gly Gly
            530                 535                 540

ATA CTC CGA AGA ACA ACT AAT GGC ACA TTT GGA ACG TTA AGA GTA ACG       2341
Ile Leu Arg Arg Thr Thr Asn Gly Thr Phe Gly Thr Leu Arg Val Thr
        545                 550                 555

GTT AAT TCA CCA TTA ACA CAA CAA TAT CGC CTA AGA GTT CGT TTT GCC       2389
Val Asn Ser Pro Leu Thr Gln Gln Tyr Arg Leu Arg Val Arg Phe Ala
    560                 565                 570

TCA ACA GGA AAT TTC AGT ATA AGG GTA CTC CGT GGA GGG GTT TCT ATC       2437
Ser Thr Gly Asn Phe Ser Ile Arg Val Leu Arg Gly Gly Val Ser Ile
575                 580                 585                 590

GGT GAT GTT AGA TTA GGG AGC ACA ATG AAC AGA GGG CAG GAA CTA ACT       2485
Gly Asp Val Arg Leu Gly Ser Thr Met Asn Arg Gly Gln Glu Leu Thr
                595                 600                 605

TAC GAA TCC TTT TTC ACA AGA GAG TTT ACT ACT ACT GGT CCG TTC AAT       2533
Tyr Glu Ser Phe Phe Thr Arg Glu Phe Thr Thr Thr Gly Pro Phe Asn
            610                 615                 620

CCG CCT TTT ACA TTT ACA CAA GCT CAA GAG ATT CTA ACA GTG AAT GCA       2581
Pro Pro Phe Thr Phe Thr Gln Ala Gln Glu Ile Leu Thr Val Asn Ala
        625                 630                 635

GAA GGT GTT AGC ACC GGT GGT GAA TAT TAT ATA GAT AGA ATT GAA ATT       2629
Glu Gly Val Ser Thr Gly Gly Glu Tyr Tyr Ile Asp Arg Ile Glu Ile
    640                 645                 650

GTC CCT GTG AAT CCG GCA CGA GAA GCG GAA GAG GAT TTA GAA GCG GCG       2677
Val Pro Val Asn Pro Ala Arg Glu Ala Glu Glu Asp Leu Glu Ala Ala
655                 660                 665                 670

AAG AAA GCG GTG GCG AGC TTG TTT ACA CGT ACA AGG GAC GGA TTA CAG       2725
```

```
                                                                    -continued Lys Lys Ala Val Ala Ser Leu Phe Thr Arg Thr Arg Asp Gly Leu Gln
            675                 680                 685

GTA AAT GTG ACA GAT TAT CAA GTG GAC CAA GCG GCA AAT TTA GTG TCA        2773
Val Asn Val Thr Asp Tyr Gln Val Asp Gln Ala Ala Asn Leu Val Ser
            690                 695                 700

TGC TTA TCC GAT GAA CAA TAT GGG CAT GAC AAA AAG ATG TTA TTG GAA        2821
Cys Leu Ser Asp Glu Gln Tyr Gly His Asp Lys Lys Met Leu Leu Glu
            705                 710                 715

GCG GTA AGA GCG GCA AAA CGC CTC AGC CGC GAA CGC AAC TTA CTT CAA        2869
Ala Val Arg Ala Ala Lys Arg Leu Ser Arg Glu Arg Asn Leu Leu Gln
            720                 725                 730

GAT CCA GAT TTT AAT ACA ATC AAT AGT ACA GAA GAG AAT GGC TGG AAG        2917
Asp Pro Asp Phe Asn Thr Ile Asn Ser Thr Glu Glu Asn Gly Trp Lys
735                 740                 745                 750

GCA AGT AAC GGT GTT ACT ATT AGC GAG GGC GGT CCA TTC TTT AAA GGT        2965
Ala Ser Asn Gly Val Thr Ile Ser Glu Gly Gly Pro Phe Phe Lys Gly
                755                 760                 765

CGT GCA CTT CAG TTA GCA AGC GCA AGA GAA AAT TAT CCA ACA TAC ATT        3013
Arg Ala Leu Gln Leu Ala Ser Ala Arg Glu Asn Tyr Pro Thr Tyr Ile
                770                 775                 780

TAT CAA AAA GTA GAT GCA TCG GTG TTA AAG CCT TAT ACA CGC TAT AGA        3061
Tyr Gln Lys Val Asp Ala Ser Val Leu Lys Pro Tyr Thr Arg Tyr Arg
                785                 790                 795

CTA GAT GGA TTT GTG AAG AGT AGT CAA GAT TTA GAA ATT GAT CTC ATC        3109
Leu Asp Gly Phe Val Lys Ser Ser Gln Asp Leu Glu Ile Asp Leu Ile
800                 805                 810

CAC CAT CAT AAA GTC CAT CTT GTA AAA AAT GTA CCA GAT AAT TTA GTA        3157
His His His Lys Val His Leu Val Lys Asn Val Pro Asp Asn Leu Val
815                 820                 825                 830

TCT GAT ACT TAC TCA GAT GGT TCT TGC AGC GGA ATC AAC CGT TGT GAT        3205
Ser Asp Thr Tyr Ser Asp Gly Ser Cys Ser Gly Ile Asn Arg Cys Asp
                835                 840                 845

GAA CAG CAT CAG GTA GAT ATG CAG CTA GAT GCG GAG CAT CAT CCA ATG        3253
Glu Gln His Gln Val Asp Met Gln Leu Asp Ala Glu His His Pro Met
                850                 855                 860

GAT TGC TGT GAA GCG GCT CAA ACA CAT GAG TTT TCT TCC TAT ATT AAT        3301
Asp Cys Cys Glu Ala Ala Gln Thr His Glu Phe Ser Ser Tyr Ile Asn
                865                 870                 875

ACA GGG GAT CTA AAT GCA AGT GTA GAT CAG GGC ATT TGG GTT GTA TTA        3349
Thr Gly Asp Leu Asn Ala Ser Val Asp Gln Gly Ile Trp Val Val Leu
880                 885                 890

AAA GTT CGA ACA ACA GAT GGG TAT GCG ACG TTA GGA AAT CTT GAA TTG        3397
Lys Val Arg Thr Thr Asp Gly Tyr Ala Thr Leu Gly Asn Leu Glu Leu
895                 900                 905                 910

GTA GAG GTT GGG CCA TTA TCG GGT GAA TCT CTA GAA CGG GAA CAA AGA        3445
Val Glu Val Gly Pro Leu Ser Gly Glu Ser Leu Glu Arg Glu Gln Arg
                915                 920                 925

GAT AAT GCG AAA TGG AAT GCA GAG CTA GGA AGA AAA CGT GCA GAA ATA        3493
Asp Asn Ala Lys Trp Asn Ala Glu Leu Gly Arg Lys Arg Ala Glu Ile
                930                 935                 940

GAT CGT GTG TAT TTA GCT GCG AAA CAA GCA ATT AAT CAT CTG TTT GTA        3541
Asp Arg Val Tyr Leu Ala Ala Lys Gln Ala Ile Asn His Leu Phe Val
                945                 950                 955

GAC TAT CAA GAT CAA CAA TTA AAT CCA GAA ATT GGG CTA GCA GAA ATT        3589
Asp Tyr Gln Asp Gln Gln Leu Asn Pro Glu Ile Gly Leu Ala Glu Ile
                960                 965                 970

AAT GAA GCT TCA AAT CTT GTA GAG TCA ATT TCG GGT GTA TAT AGT GAT        3637
Asn Glu Ala Ser Asn Leu Val Glu Ser Ile Ser Gly Val Tyr Ser Asp
975                 980                 985                 990
```

```
ACA CTA TTA CAG ATT CCT GGG ATT AAC TAC GAA ATT TAC ACA GAG TTA       3685
Thr Leu Leu Gln Ile Pro Gly Ile Asn Tyr Glu Ile Tyr Thr Glu Leu
            995                 1000                1005

TCC GAT CGC TTA CAA CAA GCA TCG TAT CTG TAT ACG TCT AGA AAT GCG       3733
Ser Asp Arg Leu Gln Gln Ala Ser Tyr Leu Tyr Thr Ser Arg Asn Ala
            1010                1015                1020

GTG CAA AAT GGA GAC TTT AAC AGT GGT CTA GAT AGT TGG AAT ACA ACT       3781
Val Gln Asn Gly Asp Phe Asn Ser Gly Leu Asp Ser Trp Asn Thr Thr
            1025                1030                1035

ATG GAT GCA TCG GTT CAG CAA GAT GGC AAT ATG CAT TTC TTA GTT CTT       3829
Met Asp Ala Ser Val Gln Gln Asp Gly Asn Met His Phe Leu Val Leu
            1040                1045                1050

TCG CAT TGG GAT GCA CAA GTT TCC CAA CAA TTG AGA GTA AAT CCG AAT       3877
Ser His Trp Asp Ala Gln Val Ser Gln Gln Leu Arg Val Asn Pro Asn
1055                1060                1065                1070

TGT AAG TAT GTC TTA CGT GTG ACA GCA AGA AAA GTA GGA GGC GGA GAT       3925
Cys Lys Tyr Val Leu Arg Val Thr Ala Arg Lys Val Gly Gly Gly Asp
                1075                1080                1085

GGA TAC GTC ACA ATC CGA GAT GGC GCT CAT CAC CAA GAA ACT CTT ACA       3973
Gly Tyr Val Thr Ile Arg Asp Gly Ala His His Gln Glu Thr Leu Thr
                1090                1095                1100

TTT AAT GCA TGT GAC TAC GAT GTA AAT GGT ACG TAT GTC AAT GAC AAT       4021
Phe Asn Ala Cys Asp Tyr Asp Val Asn Gly Thr Tyr Val Asn Asp Asn
                1105                1110                1115

TCG TAT ATA ACA GAA GAA GTG GTA TTC TAC CCA GAG ACA AAA CAT ATG       4069
Ser Tyr Ile Thr Glu Glu Val Val Phe Tyr Pro Glu Thr Lys His Met
            1120                1125                1130

TGG GTA GAG GTG AGT GAA TCC GAA GGT TCA TTC TAT ATA GAC AGT ATT       4117
Trp Val Glu Val Ser Glu Ser Glu Gly Ser Phe Tyr Ile Asp Ser Ile
1135                1140                1145                1150

GAG TTT ATT GAA ACA CAA GAG TAGAAGAGGG GGATCCTAAC GTATAGCAAC          4168
Glu Phe Ile Glu Thr Gln Glu
            1155

TATGAGAGGA TACTCCGTAC AAACAAAGAT TAAAAAAAGG TAAAATGAAT AGAACCCCCT     4228

ACTGGTAGAA GGACCGATAG GGGGTTCTTA CATGAAAAAA TGTAGCTGTT TACTAAGGTG     4288

TATAAAAAAC AGCATATCTG ATAGAAAAAA GTGAGTACCT TATAAAGAAA GAATTC         4344

(2) INFORMATION FOR SEQ ID NO: 5:

(i) SEQUENCE CHARACTERISTICS:
        (A) LENGTH: 1157 amino acids
        (B) TYPE: amino acid
        (D) TOPOLOGY: linear (ii) MOLECULE TYPE: protein (xi) SEQUENCE DESCRIPTION: SEQ ID NO: 5:

Met Asn Arg Asn Asn Gln Asn Glu Tyr Glu Ile Ile Asp Ala Pro His
1               5                   10                  15

Cys Gly Cys Pro Ser Asp Asp Val Arg Tyr Pro Leu Ala Ser Asp
                20                  25                  30

Pro Asn Ala Ala Leu Gln Asn Met Asn Tyr Lys Asp Tyr Leu Gln Met
            35                  40                  45

Thr Asp Glu Asp Tyr Thr Asp Ser Tyr Ile Asn Pro Ser Leu Ser Ile
    50                  55                  60

Ser Gly Arg Asp Ala Val Gln Thr Ala Leu Thr Val Val Gly Arg Ile
65                  70                  75                  80

Leu Gly Ala Leu Gly Val Pro Phe Ser Gly Gln Ile Val Ser Phe Tyr
                85                  90                  95
```

```
Gln Phe Leu Leu Asn Thr Leu Trp Pro Val Asn Asp Thr Ala Ile Trp
            100                 105                 110

Glu Ala Phe Met Arg Gln Val Glu Glu Leu Val Asn Gln Gln Ile Thr
        115                 120                 125

Glu Phe Ala Arg Asn Gln Ala Leu Ala Arg Leu Gln Gly Leu Gly Asp
    130                 135                 140

Ser Phe Asn Val Tyr Gln Arg Ser Leu Gln Asn Trp Leu Ala Asp Arg
145                 150                 155                 160

Asn Asp Thr Arg Asn Leu Ser Val Val Arg Ala Gln Phe Ile Ala Leu
                165                 170                 175

Asp Leu Asp Phe Val Asn Ala Ile Pro Leu Phe Ala Val Asn Gly Gln
            180                 185                 190

Gln Val Pro Leu Leu Ser Val Tyr Ala Gln Ala Val Asn Leu His Leu
        195                 200                 205

Leu Leu Leu Lys Asp Ala Ser Leu Phe Gly Glu Gly Trp Gly Phe Thr
    210                 215                 220

Gln Gly Glu Ile Ser Thr Tyr Tyr Asp Arg Gln Leu Glu Leu Thr Ala
225                 230                 235                 240

Lys Tyr Thr Asn Tyr Cys Glu Thr Trp Tyr Asn Thr Gly Leu Asp Arg
                245                 250                 255

Leu Arg Gly Thr Asn Thr Glu Ser Trp Leu Arg Tyr His Gln Phe Arg
            260                 265                 270

Arg Glu Met Thr Leu Val Val Leu Asp Val Val Ala Leu Phe Pro Tyr
        275                 280                 285

Tyr Asp Val Arg Leu Tyr Pro Thr Gly Ser Asn Pro Gln Leu Thr Arg
    290                 295                 300

Glu Val Tyr Thr Asp Pro Ile Val Phe Asn Pro Pro Ala Asn Val Gly
305                 310                 315                 320

Leu Cys Arg Arg Trp Gly Thr Asn Pro Tyr Asn Thr Phe Ser Glu Leu
                325                 330                 335

Glu Asn Ala Phe Ile Arg Pro Pro His Leu Phe Asp Arg Leu Asn Ser
            340                 345                 350

Leu Thr Ile Ser Ser Asn Arg Phe Pro Val Ser Ser Asn Phe Met Asp
        355                 360                 365

Tyr Trp Ser Gly His Thr Leu Arg Arg Ser Tyr Leu Asn Asp Ser Ala
    370                 375                 380

Val Gln Glu Asp Ser Tyr Gly Leu Ile Thr Thr Thr Arg Ala Thr Ile
385                 390                 395                 400

Asn Pro Gly Val Asp Gly Thr Asn Arg Ile Glu Ser Thr Ala Val Asp
                405                 410                 415

Phe Arg Ser Ala Leu Ile Gly Ile Tyr Gly Val Asn Arg Ala Ser Phe
            420                 425                 430

Val Pro Gly Gly Leu Phe Asn Gly Thr Thr Ser Pro Ala Asn Gly Gly
        435                 440                 445

Cys Arg Asp Leu Tyr Asp Thr Asn Asp Glu Leu Pro Pro Asp Glu Ser
    450                 455                 460

Thr Gly Ser Ser Thr His Arg Leu Ser His Val Thr Phe Phe Ser Phe
465                 470                 475                 480

Gln Thr Asn Gln Ala Gly Ser Ile Ala Asn Ala Gly Ser Val Pro Thr
                485                 490                 495

Tyr Val Trp Thr Arg Arg Asp Val Asp Leu Asn Asn Thr Ile Thr Pro
            500                 505                 510
```

-continued

Asn Arg Ile Thr Gln Leu Pro Leu Val Lys Ala Ser Ala Pro Val Ser
    515                 520                 525
Gly Thr Thr Val Leu Lys Gly Pro Gly Phe Thr Gly Gly Ile Leu
    530                 535                 540
Arg Arg Thr Thr Asn Gly Thr Phe Gly Thr Leu Arg Val Thr Val Asn
545                 550                 555                 560
Ser Pro Leu Thr Gln Gln Tyr Arg Leu Arg Val Arg Phe Ala Ser Thr
                565                 570                 575
Gly Asn Phe Ser Ile Arg Val Leu Arg Gly Gly Val Ser Ile Gly Asp
            580                 585                 590
Val Arg Leu Gly Ser Thr Met Asn Arg Gly Gln Glu Leu Thr Tyr Glu
            595                 600                 605
Ser Phe Phe Thr Arg Glu Phe Thr Thr Gly Pro Phe Asn Pro Pro
    610                 615                 620
Phe Thr Phe Thr Gln Ala Gln Glu Ile Leu Thr Val Asn Ala Glu Gly
625                 630                 635                 640
Val Ser Thr Gly Gly Glu Tyr Tyr Ile Asp Arg Ile Glu Ile Val Pro
                645                 650                 655
Val Asn Pro Ala Arg Glu Ala Glu Glu Asp Leu Glu Ala Ala Lys Lys
            660                 665                 670
Ala Val Ala Ser Leu Phe Thr Arg Thr Arg Asp Gly Leu Gln Val Asn
            675                 680                 685
Val Thr Asp Tyr Gln Val Asp Gln Ala Ala Asn Leu Val Ser Cys Leu
    690                 695                 700
Ser Asp Glu Gln Tyr Gly His Asp Lys Lys Met Leu Leu Glu Ala Val
705                 710                 715                 720
Arg Ala Ala Lys Arg Leu Ser Arg Glu Arg Asn Leu Leu Gln Asp Pro
                725                 730                 735
Asp Phe Asn Thr Ile Asn Ser Thr Glu Glu Asn Gly Trp Lys Ala Ser
            740                 745                 750
Asn Gly Val Thr Ile Ser Glu Gly Gly Pro Phe Phe Lys Gly Arg Ala
            755                 760                 765
Leu Gln Leu Ala Ser Ala Arg Glu Asn Tyr Pro Thr Tyr Ile Tyr Gln
    770                 775                 780
Lys Val Asp Ala Ser Val Leu Lys Pro Tyr Thr Arg Tyr Arg Leu Asp
785                 790                 795                 800
Gly Phe Val Lys Ser Ser Gln Asp Leu Glu Ile Asp Leu Ile His His
                805                 810                 815
His Lys Val His Leu Val Lys Asn Val Pro Asp Asn Leu Val Ser Asp
            820                 825                 830
Thr Tyr Ser Asp Gly Ser Cys Ser Gly Ile Asn Arg Cys Asp Glu Gln
            835                 840                 845
His Gln Val Asp Met Gln Leu Asp Ala Glu His His Pro Met Asp Cys
    850                 855                 860
Cys Glu Ala Ala Gln Thr His Glu Phe Ser Ser Tyr Ile Asn Thr Gly
865                 870                 875                 880
Asp Leu Asn Ala Ser Val Asp Gln Gly Ile Trp Val Leu Lys Val
                885                 890                 895
Arg Thr Thr Asp Gly Tyr Ala Thr Leu Gly Asn Leu Glu Leu Val Glu
            900                 905                 910
Val Gly Pro Leu Ser Gly Glu Ser Leu Glu Arg Glu Gln Arg Asp Asn
    915                 920                 925
Ala Lys Trp Asn Ala Glu Leu Gly Arg Lys Arg Ala Glu Ile Asp Arg

```
                930              935              940
Val Tyr Leu Ala Ala Lys Gln Ala Ile Asn His Leu Phe Val Asp Tyr
945              950              955              960

Gln Asp Gln Gln Leu Asn Pro Glu Ile Gly Leu Ala Glu Ile Asn Glu
                 965              970              975

Ala Ser Asn Leu Val Glu Ser Ile Ser Gly Val Tyr Ser Asp Thr Leu
                 980              985              990

Leu Gln Ile Pro Gly Ile Asn Tyr Glu Ile Tyr Thr Glu Leu Ser Asp
             995             1000             1005

Arg Leu Gln Gln Ala Ser Tyr Leu Tyr Thr Ser Arg Asn Ala Val Gln
            1010             1015             1020

Asn Gly Asp Phe Asn Ser Gly Leu Asp Ser Trp Asn Thr Thr Met Asp
1025             1030             1035             1040

Ala Ser Val Gln Gln Asp Gly Asn Met His Phe Leu Val Leu Ser His
                1045             1050             1055

Trp Asp Ala Gln Val Ser Gln Gln Leu Arg Val Asn Pro Asn Cys Lys
                1060             1065             1070

Tyr Val Leu Arg Val Thr Ala Arg Lys Val Gly Gly Asp Gly Tyr
    1075             1080             1085

Val Thr Ile Arg Asp Gly Ala His His Gln Glu Thr Leu Thr Phe Asn
    1090             1095             1100

Ala Cys Asp Tyr Asp Val Asn Gly Thr Tyr Val Asn Asp Asn Ser Tyr
1105             1110             1115             1120

Ile Thr Glu Glu Val Val Phe Tyr Pro Glu Thr Lys His Met Trp Val
                1125             1130             1135

Glu Val Ser Glu Ser Glu Gly Ser Phe Tyr Ile Asp Ser Ile Glu Phe
                1140             1145             1150

Ile Glu Thr Gln Glu
        1155

(2) INFORMATION FOR SEQ ID NO: 6:

(i) SEQUENCE CHARACTERISTICS:
        (A) LENGTH: 1897 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
         (A) ORGANISM: Bacillus thuringiensis (ix) FEATURE:
         (A) NAME/KEY: CDS
         (B) LOCATION: 13..1887

(ix) FEATURE:
         (A) NAME/KEY: misc_feature
         (B) LOCATION: 13..1887
         (D) OTHER INFORMATION: /note= "artificial DNA sequence of
             the bTS02618A gene, encoding the BTS02618A
             protein"

(xi) SEQUENCE DESCRIPTION: SEQ ID NO: 6:

GGTACCAAAA CC ATG GCT GAC TAC CTG CAG ATG ACC GAC GAG GAC TAC         48
          Met Ala Asp Tyr Leu Gln Met Thr Asp Glu Asp Tyr
            1               5              10

ACC GAC AGC TAC ATC AAC CCC AGC CTG AGC ATC AGC GGT CGC GAC GCC       96
Thr Asp Ser Tyr Ile Asn Pro Ser Leu Ser Ile Ser Gly Arg Asp Ala
     15                  20                  25
```

```
                                                          -continued

GTG CAG ACC GCT CTG ACC GTG GTG GGT CGC ATC CTG GGT GCC CTG GGC    144
Val Gln Thr Ala Leu Thr Val Val Gly Arg Ile Leu Gly Ala Leu Gly
     30                  35                  40

GTG CCC TTC AGC GGT CAG ATC GTG AGC TTC TAC CAG TTC CTG CTG AAC    192
Val Pro Phe Ser Gly Gln Ile Val Ser Phe Tyr Gln Phe Leu Leu Asn
 45                  50                  55                  60

ACC CTG TGG CCA GTG AAC GAC ACC GCC ATC TGG GAA GCT TTC ATG CGC    240
Thr Leu Trp Pro Val Asn Asp Thr Ala Ile Trp Glu Ala Phe Met Arg
                 65                  70                  75

CAG GTG GAG GAG CTG GTG AAC CAG CAG ATC ACC GAG TTC GCT CGC AAC    288
Gln Val Glu Glu Leu Val Asn Gln Gln Ile Thr Glu Phe Ala Arg Asn
             80                  85                  90

CAG GCC CTG GCT CGC CTG CAG GGC CTG GGC GAC AGC TTC AAC GTG TAC    336
Gln Ala Leu Ala Arg Leu Gln Gly Leu Gly Asp Ser Phe Asn Val Tyr
         95                 100                 105

CAG CGC AGC CTG CAG AAC TGG CTG GCC GAC CGC AAC GAC ACC CGC AAC    384
Gln Arg Ser Leu Gln Asn Trp Leu Ala Asp Arg Asn Asp Thr Arg Asn
    110                 115                 120

CTG AGC GTG GTG AGG GCC CAG TTC ATC GCC CTG GAC CTG GAC TTC GTG    432
Leu Ser Val Val Arg Ala Gln Phe Ile Ala Leu Asp Leu Asp Phe Val
125                 130                 135                 140

AAC GCC ATC CCC CTG TTC GCC GTG AAC GGC CAG CAG GTG CCC CTG CTG    480
Asn Ala Ile Pro Leu Phe Ala Val Asn Gly Gln Gln Val Pro Leu Leu
                145                 150                 155

AGC GTG TAC GCC CAG GCC GTG AAC CTG CAC CTG CTG CTG AAG GAT        528
Ser Val Tyr Ala Gln Ala Val Asn Leu His Leu Leu Leu Lys Asp
            160                 165                 170

GCA TCC CTG TTC GGC GAG GGC TGG GGC TTC ACC CAG GGC GAG ATC AGC    576
Ala Ser Leu Phe Gly Glu Gly Trp Gly Phe Thr Gln Gly Glu Ile Ser
        175                 180                 185

ACC TAC TAC GAC CGC CAG CTC GAG CTG ACC GCC AAG TAC ACC AAC TAC    624
Thr Tyr Tyr Asp Arg Gln Leu Glu Leu Thr Ala Lys Tyr Thr Asn Tyr
    190                 195                 200

TGC GAG ACC TGG TAC AAC ACC GGT CTG GAC CGC CTG AGG GGC ACC AAC    672
Cys Glu Thr Trp Tyr Asn Thr Gly Leu Asp Arg Leu Arg Gly Thr Asn
205                 210                 215                 220

ACC GAG AGC TGG CTG CGC TAC CAC CAG TTC CGC AGG GAG ATG ACC CTG    720
Thr Glu Ser Trp Leu Arg Tyr His Gln Phe Arg Arg Glu Met Thr Leu
                225                 230                 235

GTG GTG CTG GAC GTG GTG GCC CTG TTC CCC TAC TAC GAC GTG CGC CTG    768
Val Val Leu Asp Val Val Ala Leu Phe Pro Tyr Tyr Asp Val Arg Leu
            240                 245                 250

TAC CCC ACC GGC AGC AAC CCC CAG CTG ACA CGT GAG GTG TAC ACC GAC    816
Tyr Pro Thr Gly Ser Asn Pro Gln Leu Thr Arg Glu Val Tyr Thr Asp
        255                 260                 265

CCC ATC GTG TTC AAC CCA CCA GCC AAC GTG GGC CTG TGC CGC AGG TGG    864
Pro Ile Val Phe Asn Pro Pro Ala Asn Val Gly Leu Cys Arg Arg Trp
    270                 275                 280

GGC ACC AAC CCC TAC AAC ACC TTC AGC GAG CTG GAG AAC GCC TTC ATC    912
Gly Thr Asn Pro Tyr Asn Thr Phe Ser Glu Leu Glu Asn Ala Phe Ile
285                 290                 295                 300

AGG CCA CCC CAC CTG TTC GAC CGC CTG AAC AGC CTG ACC ATC AGC AGC    960
Arg Pro Pro His Leu Phe Asp Arg Leu Asn Ser Leu Thr Ile Ser Ser
                305                 310                 315

AAT CGA TTC CCC GTG AGC AGC AAC TTC ATG GAC TAC TGG AGC GGT CAC   1008
Asn Arg Phe Pro Val Ser Ser Asn Phe Met Asp Tyr Trp Ser Gly His
            320                 325                 330

ACC CTG CGC AGG AGC TAC CTG AAC GAC AGC GCC GTG CAG GAG GAC AGC   1056
Thr Leu Arg Arg Ser Tyr Leu Asn Asp Ser Ala Val Gln Glu Asp Ser
        335                 340                 345
```

```
TAC GGC CTG ATC ACC ACC ACC AGG GCC ACC ATC AAC CCA GGC GTG GAC      1104
Tyr Gly Leu Ile Thr Thr Thr Arg Ala Thr Ile Asn Pro Gly Val Asp
    350             355                 360

GGC ACC AAC CGC ATC GAG AGC ACC GCT GTG GAC TTC CGC AGC GCT CTG      1152
Gly Thr Asn Arg Ile Glu Ser Thr Ala Val Asp Phe Arg Ser Ala Leu
365                 370                 375                 380

ATC GGC ATC TAC GGC GTG AAC AGG GCC AGC TTC GTG CCA GGT GGC CTG      1200
Ile Gly Ile Tyr Gly Val Asn Arg Ala Ser Phe Val Pro Gly Gly Leu
                385                 390                 395

TTC AAC GGC ACC ACC AGC CCA GCC AAC GGT GGC TGC CGA GAT CTG TAC      1248
Phe Asn Gly Thr Thr Ser Pro Ala Asn Gly Gly Cys Arg Asp Leu Tyr
            400                 405                 410

GAC ACC AAC GAC GAG CTG CCA CCC GAC GAG AGC ACC GGC AGC AGC ACC      1296
Asp Thr Asn Asp Glu Leu Pro Pro Asp Glu Ser Thr Gly Ser Ser Thr
                415                 420                 425

CAC CGC CTG AGC CAC GTC ACC TTC TTC AGC TTC CAG ACC AAC CAG GCT      1344
His Arg Leu Ser His Val Thr Phe Phe Ser Phe Gln Thr Asn Gln Ala
    430                 435                 440

GGC AGC ATC GCC AAC GCT GGC AGC GTG CCC ACC TAC GTG TGG ACC AGG      1392
Gly Ser Ile Ala Asn Ala Gly Ser Val Pro Thr Tyr Val Trp Thr Arg
445                 450                 455                 460

AGG GAC GTG GAC CTG AAC AAC ACC ATC ACC CCC AAC CGC ATC ACC CAG      1440
Arg Asp Val Asp Leu Asn Asn Thr Ile Thr Pro Asn Arg Ile Thr Gln
                465                 470                 475

CTG CCC CTG GTG AAG GCC AGC GCT CCC GTG AGC GGC ACC ACC GTG CTG      1488
Leu Pro Leu Val Lys Ala Ser Ala Pro Val Ser Gly Thr Thr Val Leu
            480                 485                 490

AAG GGT CCA GGC TTC ACC GGT GGC GGT ATA CTG CGC AGG ACC ACC AAC      1536
Lys Gly Pro Gly Phe Thr Gly Gly Gly Ile Leu Arg Arg Thr Thr Asn
                495                 500                 505

GGC ACC TTC GGC ACC CTG CGC GTG ACC GTG AAT TCC CCA CTG ACC CAG      1584
Gly Thr Phe Gly Thr Leu Arg Val Thr Val Asn Ser Pro Leu Thr Gln
    510                 515                 520

CAG TAC CGC CTG CGC GTG CGC TTC GCC AGC ACC GGC AAC TTC AGC ATC      1632
Gln Tyr Arg Leu Arg Val Arg Phe Ala Ser Thr Gly Asn Phe Ser Ile
525                 530                 535                 540

CGC GTG CTG AGG GGT GGC GTG AGC ATC GGC GAC GTG CGC CTG GGC AGC      1680
Arg Val Leu Arg Gly Gly Val Ser Ile Gly Asp Val Arg Leu Gly Ser
                545                 550                 555

ACC ATG AAC AGG GGC CAG GAG CTG ACC TAC GAG AGC TTC TTC ACC CGC      1728
Thr Met Asn Arg Gly Gln Glu Leu Thr Tyr Glu Ser Phe Phe Thr Arg
            560                 565                 570

GAG TTC ACC ACC ACC GGT CCC TTC AAC CCA CCC TTC ACC TTC ACC CAG      1776
Glu Phe Thr Thr Thr Gly Pro Phe Asn Pro Pro Phe Thr Phe Thr Gln
                575                 580                 585

GCC CAG GAG ATC CTG ACC GTG AAC GCC GAG GGC GTG AGC ACC GGT GGC      1824
Ala Gln Glu Ile Leu Thr Val Asn Ala Glu Gly Val Ser Thr Gly Gly
    590                 595                 600

GAG TAC TAC ATC GAC CGC ATC GAG ATC GTG CCC GTG AAC CCA GCT CGC      1872
Glu Tyr Tyr Ile Asp Arg Ile Glu Ile Val Pro Val Asn Pro Ala Arg
605                 610                 615                 620

GAG GCC GAG GAG GAC TGAGGCTAGC                                       1897
Glu Ala Glu Glu Asp
                625
```

(2) INFORMATION FOR SEQ ID NO: 7:

(i) SEQUENCE CHARACTERISTICS:
        (A) LENGTH: 625 amino acids
        (B) TYPE: amino acid (D) TOPOLOGY: linear (ii) MOLECULE TYPE: protein (xi) SEQUENCE DESCRIPTION: SEQ ID NO: 7:

```
Met Ala Asp Tyr Leu Gln Met Thr Asp Glu Asp Tyr Thr Asp Ser Tyr
 1               5                  10                  15
Ile Asn Pro Ser Leu Ser Ile Ser Gly Arg Asp Ala Val Gln Thr Ala
            20                  25                  30
Leu Thr Val Val Gly Arg Ile Leu Gly Ala Leu Gly Val Pro Phe Ser
            35                  40                  45
Gly Gln Ile Val Ser Phe Tyr Gln Phe Leu Leu Asn Thr Leu Trp Pro
 50                  55                  60
Val Asn Asp Thr Ala Ile Trp Glu Ala Phe Met Arg Gln Val Glu Glu
 65                  70                  75                  80
Leu Val Asn Gln Gln Ile Thr Glu Phe Ala Arg Asn Gln Ala Leu Ala
            85                  90                  95
Arg Leu Gln Gly Leu Gly Asp Ser Phe Asn Val Tyr Gln Arg Ser Leu
               100                 105                 110
Gln Asn Trp Leu Ala Asp Arg Asn Asp Thr Arg Asn Leu Ser Val Val
           115                 120                 125
Arg Ala Gln Phe Ile Ala Leu Asp Leu Asp Phe Val Asn Ala Ile Pro
130                 135                 140
Leu Phe Ala Val Asn Gly Gln Gln Val Pro Leu Leu Ser Val Tyr Ala
145                 150                 155                 160
Gln Ala Val Asn Leu His Leu Leu Leu Lys Asp Ala Ser Leu Phe
           165                 170                 175
Gly Glu Gly Trp Gly Phe Thr Gln Gly Glu Ile Ser Thr Tyr Tyr Asp
               180                 185                 190
Arg Gln Leu Glu Leu Thr Ala Lys Tyr Thr Asn Tyr Cys Glu Thr Trp
           195                 200                 205
Tyr Asn Thr Gly Leu Asp Arg Leu Arg Gly Thr Asn Thr Glu Ser Trp
           210                 215                 220
Leu Arg Tyr His Gln Phe Arg Arg Glu Met Thr Leu Val Val Leu Asp
225                 230                 235                 240
Val Val Ala Leu Phe Pro Tyr Tyr Asp Val Arg Leu Tyr Pro Thr Gly
               245                 250                 255
Ser Asn Pro Gln Leu Thr Arg Glu Val Tyr Thr Asp Pro Ile Val Phe
           260                 265                 270
Asn Pro Pro Ala Asn Val Gly Leu Cys Arg Arg Trp Gly Thr Asn Pro
           275                 280                 285
Tyr Asn Thr Phe Ser Glu Leu Glu Asn Ala Phe Ile Arg Pro Pro His
           290                 295                 300
Leu Phe Asp Arg Leu Asn Ser Leu Thr Ile Ser Ser Asn Arg Phe Pro
305                 310                 315                 320
Val Ser Ser Asn Phe Met Asp Tyr Trp Ser Gly His Thr Leu Arg Arg
               325                 330                 335
Ser Tyr Leu Asn Asp Ser Ala Val Gln Glu Asp Ser Tyr Gly Leu Ile
           340                 345                 350
Thr Thr Thr Arg Ala Thr Ile Asn Pro Gly Val Asp Gly Thr Asn Arg
           355                 360                 365
Ile Glu Ser Thr Ala Val Asp Phe Arg Ser Ala Leu Ile Gly Ile Tyr
370                 375                 380
Gly Val Asn Arg Ala Ser Phe Val Pro Gly Gly Leu Phe Asn Gly Thr
```

```
385                 390                 395                 400
Thr Ser Pro Ala Asn Gly Gly Cys Arg Asp Leu Tyr Asp Thr Asn Asp
                405                 410                 415

Glu Leu Pro Pro Asp Glu Ser Thr Gly Ser Ser Thr His Arg Leu Ser
                420                 425                 430

His Val Thr Phe Phe Ser Phe Gln Thr Asn Gln Ala Gly Ser Ile Ala
                435                 440                 445

Asn Ala Gly Ser Val Pro Thr Tyr Val Trp Thr Arg Arg Asp Val Asp
450                 455                 460

Leu Asn Asn Thr Ile Thr Pro Asn Arg Ile Thr Gln Leu Pro Leu Val
465                 470                 475                 480

Lys Ala Ser Ala Pro Val Ser Gly Thr Thr Val Leu Lys Gly Pro Gly
                485                 490                 495

Phe Thr Gly Gly Gly Ile Leu Arg Arg Thr Thr Asn Gly Thr Phe Gly
                500                 505                 510

Thr Leu Arg Val Thr Val Asn Ser Pro Leu Thr Gln Gln Tyr Arg Leu
                515                 520                 525

Arg Val Arg Phe Ala Ser Thr Gly Asn Phe Ser Ile Arg Val Leu Arg
                530                 535                 540

Gly Gly Val Ser Ile Gly Asp Val Arg Leu Gly Ser Thr Met Asn Arg
545                 550                 555                 560

Gly Gln Glu Leu Thr Tyr Glu Ser Phe Phe Thr Arg Glu Phe Thr Thr
                565                 570                 575

Thr Gly Pro Phe Asn Pro Pro Phe Thr Phe Thr Gln Ala Gln Glu Ile
                580                 585                 590

Leu Thr Val Asn Ala Glu Gly Val Ser Thr Gly Gly Glu Tyr Tyr Ile
                595                 600                 605

Asp Arg Ile Glu Ile Val Pro Val Asn Pro Ala Arg Glu Ala Glu Glu
                610                 615                 620

Asp
625

(2) INFORMATION FOR SEQ ID NO: 8:

(i) SEQUENCE CHARACTERISTICS:
        (A) LENGTH: 1897 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 13..1887

(ix) FEATURE:
        (A) NAME/KEY: misc_feature
        (B) LOCATION: 13..1887
        (D) OTHER INFORMATION: /note= "DNA sequence of bTS02618Aa
            gene encoding the BTS02618Aa protein"

(xi) SEQUENCE DESCRIPTION: SEQ ID NO: 8:

GGTACCAAAA CC ATG GCT GAC TAC CTG CAG ATG ACC GAC GAG GAC TAC          48
              Met Ala Asp Tyr Leu Gln Met Thr Asp Glu Asp Tyr
                1               5                   10

ACC GAC AGC TAC ATC AAC CCC AGC CTG AGC ATC AGC GGT CGC GAC GCC        96
Thr Asp Ser Tyr Ile Asn Pro Ser Leu Ser Ile Ser Gly Arg Asp Ala
            15                  20                  25

GTG CAG ACC GCT CTG ACC GTG GTG GGT CGC ATC CTG GGT GCC CTG GGC       144
```

```
                                                         -continued

Val Gln Thr Ala Leu Thr Val Val Gly Arg Ile Leu Gly Ala Leu Gly
     30                  35                  40

GTG CCC TTC AGC GGT CAG ATC GTG AGC TTC TAC CAG TTC CTG CTG AAC        192
Val Pro Phe Ser Gly Gln Ile Val Ser Phe Tyr Gln Phe Leu Leu Asn
 45                  50                  55                  60

ACC CTG TGG CCA GTG AAC GAC ACC GCC ATC TGG GAA GCT TTC ATG CGC        240
Thr Leu Trp Pro Val Asn Asp Thr Ala Ile Trp Glu Ala Phe Met Arg
                 65                  70                  75

CAG GTG GAG GAG CTG GTG AAC CAG CAG ATC ACC GAG TTC GCT CGC AAC        288
Gln Val Glu Glu Leu Val Asn Gln Gln Ile Thr Glu Phe Ala Arg Asn
                     80                  85                  90

CAG GCC CTG GCT CGC CTG CAG GGC CTG GGC GAC AGC TTC AAC GTG TAC        336
Gln Ala Leu Ala Arg Leu Gln Gly Leu Gly Asp Ser Phe Asn Val Tyr
                 95                 100                 105

CAG CGC AGC CTG CAG AAC TGG CTG GCC GAC CGC AAC GAC ACC AAG AAC        384
Gln Arg Ser Leu Gln Asn Trp Leu Ala Asp Arg Asn Asp Thr Lys Asn
            110                 115                 120

CTG AGC GTG GTG AGG GCC CAG TTC ATC GCC CTG GAC CTG GAC TTC GTG        432
Leu Ser Val Val Arg Ala Gln Phe Ile Ala Leu Asp Leu Asp Phe Val
125                 130                 135                 140

AAC GCC ATC CCC CTG TTC GCC GTG AAC GGC CAG CAG GTG CCC CTG CTG        480
Asn Ala Ile Pro Leu Phe Ala Val Asn Gly Gln Gln Val Pro Leu Leu
                145                 150                 155

AGC GTG TAC GCC CAG GCC GTG AAC CTG CAC CTG CTG CTG CTG AAG GAT        528
Ser Val Tyr Ala Gln Ala Val Asn Leu His Leu Leu Leu Leu Lys Asp
                160                 165                 170

GCA TCC CTG TTC GGC GAG GGC TGG GGC TTC ACC CAG GGC GAG ATC AGC        576
Ala Ser Leu Phe Gly Glu Gly Trp Gly Phe Thr Gln Gly Glu Ile Ser
            175                 180                 185

ACC TAC TAC GAC CGC CAG CTC GAG CTG ACC GCC AAG TAC ACC AAC TAC        624
Thr Tyr Tyr Asp Arg Gln Leu Glu Leu Thr Ala Lys Tyr Thr Asn Tyr
            190                 195                 200

TGC GAG ACC TGG TAC AAC ACC GGT CTG GAC CGC CTG AGG GGC ACC AAC        672
Cys Glu Thr Trp Tyr Asn Thr Gly Leu Asp Arg Leu Arg Gly Thr Asn
205                 210                 215                 220

ACC GAG AGC TGG CTG CGC TAC CAC CAG TTC CGC AGG GAG ATG ACC CTG        720
Thr Glu Ser Trp Leu Arg Tyr His Gln Phe Arg Arg Glu Met Thr Leu
                225                 230                 235

GTG GTG CTG GAC GTG GTG GCC CTG TTC CCC TAC TAC GAC GTG CGC CTG        768
Val Val Leu Asp Val Val Ala Leu Phe Pro Tyr Tyr Asp Val Arg Leu
                240                 245                 250

TAC CCC ACC GGC AGC AAC CCC CAG CTG ACA CGT GAG GTG TAC ACC GAC        816
Tyr Pro Thr Gly Ser Asn Pro Gln Leu Thr Arg Glu Val Tyr Thr Asp
            255                 260                 265

CCC ATC GTG TTC AAC CCA CCA GCC AAC GTG GGC CTG TGC CGC AGG TGG        864
Pro Ile Val Phe Asn Pro Pro Ala Asn Val Gly Leu Cys Arg Arg Trp
270                 275                 280

GGC ACC AAC CCC TAC AAC ACC TTC AGC GAG CTG GAG AAC GCC TTC ATC        912
Gly Thr Asn Pro Tyr Asn Thr Phe Ser Glu Leu Glu Asn Ala Phe Ile
285                 290                 295                 300

AGG CCA CCC CAC CTG TTC GAC CGC CTG AAC AGC CTG ACC ATC AGC AGC        960
Arg Pro Pro His Leu Phe Asp Arg Leu Asn Ser Leu Thr Ile Ser Ser
                305                 310                 315

AAT CGA TTC CCC GTG AGC AGC AAC TTC ATG GAC TAC TGG AGC GGT CAC       1008
Asn Arg Phe Pro Val Ser Ser Asn Phe Met Asp Tyr Trp Ser Gly His
            320                 325                 330

ACC CTG CGC AGG AGC TAC CTG AAC GAC AGC GCC GTG CAG GAG GAC AGC       1056
Thr Leu Arg Arg Ser Tyr Leu Asn Asp Ser Ala Val Gln Glu Asp Ser
            335                 340                 345
```

```
TAC GGC CTG ATC ACC ACC ACC AGG GCC ACC ATC AAC CCA GGC GTG GAC      1104
Tyr Gly Leu Ile Thr Thr Thr Arg Ala Thr Ile Asn Pro Gly Val Asp
350                 355                 360

GGC ACC AAC CGC ATC GAG AGC ACC GCT GTG GAC TTC CGC AGC GCT CTG      1152
Gly Thr Asn Arg Ile Glu Ser Thr Ala Val Asp Phe Arg Ser Ala Leu
365                 370                 375                 380

ATC GGC ATC TAC GGC GTG AAC AGG GCC AGC TTC GTG CCA GGT GGC CTG      1200
Ile Gly Ile Tyr Gly Val Asn Arg Ala Ser Phe Val Pro Gly Gly Leu
            385                 390                 395

TTC AAC GGC ACC ACC AGC CCA GCC AAC GGT GGC TGC CGA GAT CTG TAC      1248
Phe Asn Gly Thr Thr Ser Pro Ala Asn Gly Gly Cys Arg Asp Leu Tyr
            400                 405                 410

GAC ACC AAC GAC GAG CTG CCA CCC GAC GAG AGC ACC GGC AGC AGC ACC      1296
Asp Thr Asn Asp Glu Leu Pro Pro Asp Glu Ser Thr Gly Ser Ser Thr
            415                 420                 425

CAC CGC CTG AGC CAC GTC ACC TTC TTC AGC TTC CAG ACC AAC CAG GCT      1344
His Arg Leu Ser His Val Thr Phe Phe Ser Phe Gln Thr Asn Gln Ala
430                 435                 440

GGC AGC ATC GCC AAC GCT GGC AGC GTG CCC ACC TAC GTG TGG ACC AGG      1392
Gly Ser Ile Ala Asn Ala Gly Ser Val Pro Thr Tyr Val Trp Thr Arg
445                 450                 455                 460

AGG GAC GTG GAC CTG AAC AAC ACC ATC ACC CCC AAC CGC ATC ACC CAG      1440
Arg Asp Val Asp Leu Asn Asn Thr Ile Thr Pro Asn Arg Ile Thr Gln
            465                 470                 475

CTG CCC CTG GTG AAG GCC AGC GCT CCC GTG AGC GGC ACC ACC GTG CTG      1488
Leu Pro Leu Val Lys Ala Ser Ala Pro Val Ser Gly Thr Thr Val Leu
            480                 485                 490

AAG GGT CCA GGC TTC ACC GGT GGC GGT ATA CTG CGC AGG ACC ACC AAC      1536
Lys Gly Pro Gly Phe Thr Gly Gly Gly Ile Leu Arg Arg Thr Thr Asn
            495                 500                 505

GGC ACC TTC GGC ACC CTG CGC GTG ACC GTG AAT TCC CCA CTG ACC CAG      1584
Gly Thr Phe Gly Thr Leu Arg Val Thr Val Asn Ser Pro Leu Thr Gln
510                 515                 520

CAG TAC CGC CTG CGC GTG CGC TTC GCC AGC ACC GGC AAC TTC AGC ATC      1632
Gln Tyr Arg Leu Arg Val Arg Phe Ala Ser Thr Gly Asn Phe Ser Ile
525                 530                 535                 540

CGC GTG CTG AGG GGT GGC GTG AGC ATC GGC GAC GTG CGC CTG GGC AGC      1680
Arg Val Leu Arg Gly Gly Val Ser Ile Gly Asp Val Arg Leu Gly Ser
            545                 550                 555

ACC ATG AAC AGG GGC CAG GAG CTG ACC TAC GAG AGC TTC TTC ACC CGC      1728
Thr Met Asn Arg Gly Gln Glu Leu Thr Tyr Glu Ser Phe Phe Thr Arg
            560                 565                 570

GAG TTC ACC ACC ACC GGT CCC TTC AAC CCA CCC TTC ACC TTC ACC CAG      1776
Glu Phe Thr Thr Thr Gly Pro Phe Asn Pro Pro Phe Thr Phe Thr Gln
            575                 580                 585

GCC CAG GAG ATC CTG ACC GTG AAC GCC GAG GGC GTG AGC ACC GGT GGC      1824
Ala Gln Glu Ile Leu Thr Val Asn Ala Glu Gly Val Ser Thr Gly Gly
590                 595                 600

GAG TAC TAC ATC GAC CGC ATC GAG ATC GTG CCC GTG AAC CCA GCT CGC      1872
Glu Tyr Tyr Ile Asp Arg Ile Glu Ile Val Pro Val Asn Pro Ala Arg
605                 610                 615                 620

GAG GCC GAG GAG GAC TGAGGCTAGC                                       1897
Glu Ala Glu Glu Asp
                625

(2) INFORMATION FOR SEQ ID NO: 9:

(i) SEQUENCE CHARACTERISTICS:
        (A) LENGTH: 625 amino acids
        (B) TYPE: amino acid
        (D) TOPOLOGY: linear
```

(ii) MOLECULE TYPE: protein (xi) SEQUENCE DESCRIPTION: SEQ ID NO: 9:

```
Met Ala Asp Tyr Leu Gln Met Thr Asp Glu Asp Tyr Thr Asp Ser Tyr
  1               5                  10                  15

Ile Asn Pro Ser Leu Ser Ile Ser Gly Arg Asp Ala Val Gln Thr Ala
                 20                  25                  30

Leu Thr Val Val Gly Arg Ile Leu Gly Ala Leu Gly Val Pro Phe Ser
             35                  40                  45

Gly Gln Ile Val Ser Phe Tyr Gln Phe Leu Leu Asn Thr Leu Trp Pro
         50                  55                  60

Val Asn Asp Thr Ala Ile Trp Glu Ala Phe Met Arg Gln Val Glu Glu
 65                  70                  75                  80

Leu Val Asn Gln Gln Ile Thr Glu Phe Ala Arg Asn Gln Ala Leu Ala
                 85                  90                  95

Arg Leu Gln Gly Leu Gly Asp Ser Phe Asn Val Tyr Gln Arg Ser Leu
            100                 105                 110

Gln Asn Trp Leu Ala Asp Arg Asn Asp Thr Lys Asn Leu Ser Val Val
            115                 120                 125

Arg Ala Gln Phe Ile Ala Leu Asp Leu Asp Phe Val Asn Ala Ile Pro
130                 135                 140

Leu Phe Ala Val Asn Gly Gln Gln Val Pro Leu Leu Ser Val Tyr Ala
145                 150                 155                 160

Gln Ala Val Asn Leu His Leu Leu Leu Lys Asp Ala Ser Leu Phe
                165                 170                 175

Gly Glu Gly Trp Gly Phe Thr Gln Gly Glu Ile Ser Thr Tyr Tyr Asp
            180                 185                 190

Arg Gln Leu Glu Leu Thr Ala Lys Tyr Thr Asn Tyr Cys Glu Thr Trp
            195                 200                 205

Tyr Asn Thr Gly Leu Asp Arg Leu Arg Gly Thr Asn Thr Glu Ser Trp
            210                 215                 220

Leu Arg Tyr His Gln Phe Arg Arg Glu Met Thr Leu Val Val Leu Asp
225                 230                 235                 240

Val Val Ala Leu Phe Pro Tyr Tyr Asp Val Arg Leu Tyr Pro Thr Gly
                245                 250                 255

Ser Asn Pro Gln Leu Thr Arg Glu Val Tyr Thr Asp Pro Ile Val Phe
            260                 265                 270

Asn Pro Pro Ala Asn Val Gly Leu Cys Arg Arg Trp Gly Thr Asn Pro
            275                 280                 285

Tyr Asn Thr Phe Ser Glu Leu Glu Asn Ala Phe Ile Arg Pro Pro His
            290                 295                 300

Leu Phe Asp Arg Leu Asn Ser Leu Thr Ile Ser Ser Asn Arg Phe Pro
305                 310                 315                 320

Val Ser Ser Asn Phe Met Asp Tyr Trp Ser Gly His Thr Leu Arg Arg
                325                 330                 335

Ser Tyr Leu Asn Asp Ser Ala Val Gln Glu Asp Ser Tyr Gly Leu Ile
            340                 345                 350

Thr Thr Thr Arg Ala Thr Ile Asn Pro Gly Val Asp Gly Thr Asn Arg
            355                 360                 365

Ile Glu Ser Thr Ala Val Asp Phe Arg Ser Ala Leu Ile Gly Ile Tyr
            370                 375                 380

Gly Val Asn Arg Ala Ser Phe Val Pro Gly Gly Leu Phe Asn Gly Thr
385                 390                 395                 400
```

-continued

```
Thr Ser Pro Ala Asn Gly Gly Cys Arg Asp Leu Tyr Asp Thr Asn Asp
            405                 410                 415

Glu Leu Pro Pro Asp Glu Ser Thr Gly Ser Ser Thr His Arg Leu Ser
            420                 425                 430

His Val Thr Phe Phe Ser Phe Gln Thr Asn Gln Ala Gly Ser Ile Ala
            435                 440                 445

Asn Ala Gly Ser Val Pro Thr Tyr Val Trp Thr Arg Arg Asp Val Asp
    450                 455                 460

Leu Asn Asn Thr Ile Thr Pro Asn Arg Ile Thr Gln Leu Pro Leu Val
465                 470                 475                 480

Lys Ala Ser Ala Pro Val Ser Gly Thr Thr Val Leu Lys Gly Pro Gly
            485                 490                 495

Phe Thr Gly Gly Gly Ile Leu Arg Arg Thr Thr Asn Gly Thr Phe Gly
            500                 505                 510

Thr Leu Arg Val Thr Val Asn Ser Pro Leu Thr Gln Gln Tyr Arg Leu
            515                 520                 525

Arg Val Arg Phe Ala Ser Thr Gly Asn Phe Ser Ile Arg Val Leu Arg
    530                 535                 540

Gly Gly Val Ser Ile Gly Asp Val Arg Leu Gly Ser Thr Met Asn Arg
545                 550                 555                 560

Gly Gln Glu Leu Thr Tyr Glu Ser Phe Phe Thr Arg Glu Phe Thr Thr
            565                 570                 575

Thr Gly Pro Phe Asn Pro Pro Phe Thr Phe Thr Gln Ala Gln Glu Ile
            580                 585                 590

Leu Thr Val Asn Ala Glu Gly Val Ser Thr Gly Gly Glu Tyr Tyr Ile
            595                 600                 605

Asp Arg Ile Glu Ile Val Pro Val Asn Pro Ala Arg Glu Ala Glu Glu
    610                 615                 620

Asp
625
```

BACILLUS THURINGIENSIS STRAINS AND THEIR INSECTICIDAL PROTEINS

This application is a continuation divisional of application Ser. No. 09/019,809, filed on Feb. 6, 1998, now U.S. Pat. No. 6,143,550 which is a divisional of prior application Ser. No. 08/532,547, filed Dec. 6, 1995, now U.S. Pat. No. 5,861,543 application Ser. No. 08/532,547 is the national phase of PCT International Application No. PCT/EP94/00553 filed on Feb. 25, 1994 under 35 U.S.C. §371. The entire contents of each of the above-identified applications are hereby incorporated by reference.

BACKGROUND OF THE INVENTION

1. Field of the Invention

This invention relates to four novel strains of *Bacillus thuringiensis* (the "BTS02617A strain", the "BTS02618A strain", the "BTS02654B strain" and the "BTS02652E strain"), each of which produces crystallized proteins (the "BTS02617A crystal proteins", the "BTS02618A crystal proteins", the "BTS02654B crystal proteins" and the "BTS02652E crystal proteins", respectively) which are packaged in crystals (the "BTS02617A crystals", the "BTS02618A crystals", the "BTS02654B crystals" and the "BTS02652E crystals", respectively) during sporulation. The BTS02617A, BTS02618A, BTS02654B and BTS02652E strains were deposited under the provisions of the Budapest Treaty at the Belgian Coordinated Collections of Microorganisms—Collection Laboratorium voor Microbiologie Belgium ("BCCM-LMG"), R. U. G., K. Ledeganckstraat 35, B-9000 Gent.

This invention also relates to an insecticide composition that is active against Lepidoptera and that comprises the BTS02617A, BTS02618A, BTS02654B or BTS02652E strain, as such, or preferably the BTS02617A, BTS02618A, BTS02654B or BTS02652E crystals, crystal proteins or the active component(s) thereof as an active ingredient.

This invention further relates to a gene (the "bTS02618A gene"), which is present in the genome of the BTS02617A, BTS02618A, BTS02654B and BTS02652E strains and which encodes an insecticidal protein (the "BTS02618A protoxin") that is found in the BTS02617A, BTS02618A, BTS02654B and BTS02652E crystals. The BTS02618A protoxin is the protein that is produced by the BTS02617A, BTS02618A, BTS02654B and BTS02652E strains before being packaged into their respective BTS02617A, BTS02618A, BTS02654B and BTS02652E crystals.

This invention still further relates to a toxin (the "BTS02618A toxin") which can be obtained (e.g., by trypsin digestion) from the BTS02618A protoxin. The BTS02618A toxin is an insecticidally active protein which can be liberated from the BTS02617A crystals, the BTS02618A crystals, the BTS02654B crystals, and the BTS02652E crystals, which are produced by the BTS02617A strain, the BTS02618A strain, the BTS02654B strain and the BTS02652E strain, respectively. This toxin and its protoxin have a high activity against a wide range of lepidopteran insects, particularly against Noctuidae, especially against Spodoptera and Agrotis spp., but also against other important lepidopteran insects such as Pyralidae, particularly the European corn borer, *Ostrinia nubilalis*, Gelechiidae such as *Phthorimaea operculella* and Yponomeutidae such as *Plutella xylostella*. Furthermore, the BTS02618A protein is the first Bt protein with significant activity towards *Agrotis segetum*. This new characteristic of the BTS02618A protoxin and toxin ("(pro)toxin"), i.e., the combination of activity against different economically important Lepidopteran insect families such as Noctuidae, Yponomeutidae, Gelechiidae and Pyralidae, makes this (pro)toxin an ideally suited compound for combatting a wide range of insect pests by contacting these insects with the (pro)toxin, e.g., by spraying or by expressing the bTS02618A gene in plant-associated bacteria or in plants. The BTS02618A toxin is believed to represent the smallest portion of the BTS02618A protoxin which is insecticidally effective against Lepidoptera.

This invention also relates to transformed *Bacillus thuringiensis* strains, containing DNA sequences encoding a BTS02618A protein or variants thereof having substantially the same insecticidal activity.

This invention yet further relates to a chimeric gene that can be used to transform a plant cell and that contains the following operably linked DNA fragments:

1) a part of the bTS02618A gene (the "insecticidally effective bTS02618A gene part") encoding an insecticidally effective portion of the BTS02618A protoxin, preferably a truncated part of the bTS02618A gene (the "truncated bTS02618A gene") encoding just the BTS02618A toxin;

2) a promoter suitable for transcription of the insecticidally effective bTS02618A gene part in a plant cell; and 3) suitable 3' end transcript formation and polyadenylation signals for expressing the insecticidally effective bTS02618A gene part in a plant cell. This chimeric gene is hereinafter generally referred to as the "bTS02618A chimeric gene".

This invention also relates to:

1) a cell (the "transformed plant cell") of a plant, such as corn or cotton, the genome of which is transformed with the insecticidally effective bTS02618A gene part, preferably the bTS02618A chimeric gene; and 2) a plant (the "transformed plant") which is regenerated from the transformed plant cell or is produced from the so-regenerated plant and their seeds, the genome of which contains the insecticidally effective bTS02618A gene part, preferably the bTS02618A chimeric gene, and which is resistant to Lepidoptera.

This invention still further relates to:

1) a microbial organism, such as *B. thuringiensis* or Pseudomonas spp., the genome of which is transformed with all or part of the bTS02618A gene; and 2) a microbial spore, containing a genome which is transformed with all or parts of the bTS02618A gene.

Another embodiment of the present invention relates to artificially made bTS02618A genes which encode BTS02618A proteins, and to proteins which are more protease resistant than native Bt proteins, more preferably the native BTS02618A protein. A particular example of a protein that is more protease resistant is the BTS02618Aa protein. Furthermore, the present invention also relates to a DNA sequence encoding the BTS02618Aa protein.

Yet another embodiment of the present invention relates to a chimeric gene that can be used to transform a plant cell and that contains:

1) a DNA sequence encoding an insecticidally effective portion of the BTS02618Aa protoxin, preferably a truncated part of the bTS02618Aa gene (the "truncated bTS02618Aa gene") encoding just the BTS02618Aa toxin;

2) a promoter suitable for transcription of the insecticidally effective bTS02618Aa gene part in a plant cell; and 3) suitable 3' end transcript formation and polyadenylation signals for expressing the insecticidally effective bTS02618Aa gene part in a plant cell. This chimeric gene is hereinafter generally referred to as the "bTS02618Aa chimeric gene".

This invention further relates to:

1) a cell (the "transformed plant cell") of a plant, such as corn or cotton, the genome of which is transformed with the insecticidally effective bTS02618Aa gene part, preferably the bTS02618Aa chimeric gene; and 2) a plant (the "transformed plant") which is regenerated from the transformed plant cell or is produced from the so-regenerated plant and their seeds, the genome of which contains the insecticidally effective bTS02618Aa gene part, preferably the bTS02618Aa chimeric gene, and which is resistant to Lepidoptera.

This invention still further relates to:

1) a microbial organism, such as *B. thuringiensis* or Pseudomonas spp., the genome of which is transformed with all or part of a DNA sequence encoding the BTS02618Aa protein; and 2) a microbial spore, containing a genome which is transformed with all or part of the bTS02618Aa gene.

Yet another embodiment of the present invention relates to insecticidal compositions that are active against Lepidoptera and that comprise a more protease resistant Bt protein, more particularly the BTS02618Aa protein or a variant thereof which has substantially the same insecticidal activity.

2. Description of the Prior Art

*B. thuringiensis* ("Bt") is a Gram-positive bacterium which produces endogenous crystals upon sporulation. The crystals are composed of proteins which are specifically toxic against insect larvae. These crystal proteins and corresponding genes have been classified based on their structure and insecticidal spectrum (Höfte and Whiteley, 1989). The four major classes are Lepidoptera-specific (cryI), Lepidoptera- and Diptera-specific (cryII), Coleoptera-specific (cryIII), and Diptera-specific (cryIV) genes.

The fact that conventional submerged fermentation techniques can be used to produce Bt spores on a large scale makes Bt bacteria commercially attractive as a source of insecticidal compositions.

Gene fragments from some Bt strains, encoding insecticidal proteins, have heretofore been identified and integrated into plant genomes in order to render the plants insect-resistant. However, obtaining expression of such Bt gene fragments in plants is not a straightforward process. In order to achieve optimal expression of an insecticidal protein in plant cells, it has been found necessary to engineer each Bt gene fragment in a specific way so that it encodes a part of a Bt protoxin that retains substantial toxicity against its target insects (European patent application ("EPA") 86/300,291.1 and 88/402,115.5; U.S. patent application 821,582, filed Jan. 22, 1986).

SUMMARY OF THE INVENTION

In accordance with this invention, four novel Bt strains, i.e., the BTS02617A, BTS02618A, BTS02654B and BTS02652E strains, are provided. The BTS02617A, BTS02618A, BTS02654B and BTS02652E crystals and crystal proteins, the BTS02618A protoxin and toxin produced by the strains during sporulation, and insecticidally effective portions of the BTS02618A protoxin, as well as equivalents of these crystals, crystal proteins, protoxin, toxin and insecticidally effective protoxin portions, each possess insecticidal activity and can therefore be formulated into insecticidal compositions against Lepidoptera in general, and particularly against Noctuidae, such as Agrotis spp. (cutworms such as *Agrotis ipsilon* and *Agrotis segetum*), Mamestra spp. (e.g., the cabbage moth, *Mamestra brassica*) and Spodoptera spp. (armyworms, such as *Spodoptera exigua, Spodoptera frugiperda, Spodoptera littoralis* and *Spodoptera litura*), against Pyralidae (e.g., the European corn borer, *Ostrinia nubilalis*), against Gelechiidae such as *Phthorimaea operculella* and Yponomeutidae (such as *Plutella xylostella*) which are major pests of various economically important crops, such as corn, cotton and many vegetables such as Brassicas.

Also in accordance with this invention, a plant cell genome is transformed with the insecticidally effective bTS02618A gene part, preferably the truncated bTS02618A gene, or an equivalent thereof such as a modified, synthetic bTS02618A gene. It is preferred that this transformation be carried out with the bTS02618A chimeric gene. The resulting transformed plant cell can be used to produce transformed plants, seeds of transformed plants and plant cell cultures consisting essentially of the transformed cells. The transformed cells in some or all of the tissues of the transformed plants: 1) contain the insecticidally effective bTS02618A gene part as a stable insert in their genome, and 2) express the insecticidally effective bTS02618A gene part by producing an insecticidally effective portion of its BTS02618A protoxin, preferably its BTS02618A toxin, thereby rendering the plant resistant to Lepidoptera. The transformed plant cells of this invention can also be used to produce, for recovery, such insecticidal Bt proteins.

Further in accordance with this invention, a process is provided for rendering a plant resistant to Lepidoptera by transforming the plant cell genome with the insecticidally effective bTS02618A gene part, preferably the truncated bTS02618A gene, or an equivalent thereof. In this regard, it is preferred that the plant cell be transformed with the bTS02618A chimeric gene.

Yet further in accordance with this invention, there are provided the BTS02618A protoxin, the insecticidally effective portions of such protoxin and the BTS02618A toxin, as well as functional parts of the BTS02618A toxin, as well as the bTS02618A gene, the insecticidally effective bTS02618A gene part, the truncated bTS02618A gene and the chimeric bTS02618A gene, as well as their equivalents.

Also in accordance with this invention, a DNA sequence, either natural or artificial, encoding the BTS02618A protoxin or insecticidally effective portions thereof, such as the toxin, is provided.

Also in accordance with this invention are provided an insecticidal composition against Lepidoptera, particularly Noctuidae, Pyralidae, Gelechiidae and Yponomeutidae, and a method for controlling Lepidoptera, particularly Noctuidae, Pyralidae, Gelechiidae and Yponomeutidae, with the insecticidal composition, wherein the insecticidal composition comprises the BTS02617A, BTS02618A, BTS02654B or BTS02652E strain, crystals and/or crystal proteins or the BTS02618A protoxin, toxin and/or insecticidally effective protoxin portions or their equivalents.

Also in accordance with this invention, bacteria, particularly *E. coli* and *Bacillus thuringiensis*, transformed to express a DNA encoding the BTS02618A protein variant, such as the BTS02618Aa protein or more improved protease resistant Bt proteins are provided.

Furthermore, in accordance with this invention, an artificial DNA sequence encoding the BTS02618A protein, as well as new forms of Bt proteins with improved protease resistance, more particularly the BTS02618Aa or the modified BTS02618A protein are provided, and DNA sequences encoding these new proteins. Further provided are plant cells expressing an artificial DNA sequence encoding the BTS02618A toxin or Bt toxins with improved protease resistance, more preferably the BTS02618Aa toxin.

Also provided is an insecticidal composition, comprising as an active ingredient the BTS02618Aa protein, or a variant thereof with substantially the same insecticidal activity. Also provided is a method to combat Lepidopteran insects by contacting these insects with Bt proteins having improved protease resistance, more preferably the BTS02618Aa protein or a variant thereof.

More specifically provided are new Bt proteins, preferably Lepidoptera active Bt proteins, having substantially the same insecticidal activity as the native Bt protein, but characterized in their resistance to further proteolytic cleavage of the about 60 to 70 kD toxin form. Such new Bt proteins have inactivated internal protease cleavage sites, so that these proteins have increased stability while retaining substantially the same insecticidal activity. Thus, these new Bt proteins are not readily cleaved into smaller proteolytic fragments which lower their insecticidal activity upon prolonged incubation in the presence of proteases.

BRIEF DESCRIPTION OF THE DRAWING

FIG. 1 represents Southern blot analysis of AluI-digested total DNA of Bt strain HD127 (lane 1), the BTS02618A strain (lane 2), Bt strain BTS02459 (containing cryIA(c); 81k, cryIC en cryIE, lane 3), and Bt strain BTS02480E (containing the same genes as HD-127, lane 4), using a mixture of DNA-probes for cryI crystal protein genes, including the cryIG probe (SEQ ID NO:1). Each band corresponds to a particular crystal protein gene. With these probes, the BTS02618A strain is found to contain the cryIA(b) gene and a novel gene, which is the bTS02618A gene, identified by an AluI fragment of approximately 530 bp, hybridizing to the cryIG probe of SEQ ID NO:1. The names of the recognized cryI genes are indicated, as well as the size of some fragments. The bTS02618A gene is indicated with three asterisks; "?" indicates an unknown gene fragment.

DETAILED DESCRIPTION OF THE INVENTION

The BTS02618A protoxin of this invention can be isolated in a conventional manner from the BTS02617A strain, deposited on Jul. 2, 1992 at the BCCM-LMG under accession number LMG P-12592, the BTS02618A strain, deposited on Jul. 2, 1992 at the BCCM-LMG under accession number LMG P-12593, the BTS02654B strain, deposited on Jul. 2, 1992 at the BCCM-LMG under accession number LMG P-12594, or the BTS02652E strain deposited on Mar. 1, 1993 at the BCCM-LMG under accession number LMG P-13493. For example, the BTS02617A, BTS02618A, BTS02654B or BTS02652E crystals can be isolated from sporulated cultures of their respective strain (Mahillon and Delcour, 1984), and then, the BTS02618A protoxin can be isolated from the crystals according to the method of Höfte et al. (1986). The protoxins can be used to prepare monoclonal or polyclonal antibodies specific for the protoxin in a conventional manner (Höfte et al., 1988). The BTS02618A toxin can be obtained by protease (e.g., trypsin) digestion of the BTS02618A protoxin.

The bTS02618A gene can be isolated in a conventional manner. The bTS02618A gene can be identified in the BTS02617A, BTS02618A, BTS02654B or BTS02652E strain, using the procedure described in U.S. patent application 821,582, filed Jan. 22, 1986, and in EPA 86/300,291.1 and 88/402,115.5 (which are incorporated herein by reference). The bTS02618A gene was identified by: digesting total DNA from one of the above strains with restriction enzymes; size fractionating the DNA fragments, so produced, into DNA fractions of 5 to 10 Kb; ligating these fractions to cloning vectors; screening the E. coli, transformed with the cloning vectors, with a DNA probe that was constructed from a region of the cryIG gene (Smulevitch et al., 1991; Gleave et al., 1992).

The term "bTS02618A gene" as used herein includes a DNA sequence encoding the BTS02618A protoxin or toxin or functionally equivalent variants thereof. Indeed, because of the degeneracy of the genetic code, some amino acid codons can be replaced with others without changing the amino acid sequence of the protein. Furthermore, some amino acids can be substituted by other equivalent amino acids without significantly changing the insecticidal activity of the protein. Also, changes in amino acid composition in regions of the molecule, different from those responsible for binding and toxicity are less likely to cause a difference in insecticidal activity of the protein. Such equivalents of the gene include DNA sequences hybridizing to the DNA sequence of the BTS02618A toxin or protoxin of SEQ ID. No. 4 and encoding a protein with the same insecticidal characteristics as the BTS02618A (pro)toxin, of this invention. In this context, the term "hybridization" refers to conventional hybridization conditions, most preferably stringent hybridization conditions.

The "BTS02618A protein" is a general term for the BTS02618A protoxin and variants or mutants thereof with substantially the same insecticidal activity; for example, the BTS02618A or BTS02618Aa toxins.

As used herein, the term "more or improved protease resistant protein" means that the Bt protein fragment resulting from protease cleavage of the native protoxin does not result in a substantial loss of insecticidal activity due to the further cleavage of the insecticidally active toxin part of the protein. It is preferable that the insecticidally active toxin part of the protein be about 60 to 70 kD and more particularly that the further cleavage is at the N-terminal part of the toxin. It is also preferred that the protein is insecticidal for Lepidoptera.

A preferred example of an "alternative form" of the bTS02618A gene is the artificial bTS02618A gene of SEQ ID. No. 6, encoding a BTS02618A toxin. A further preferred example of an artificial bTS02618A gene is illustrated in the DNA sequence of SEQ ID. No. 8, for reasons of clarity further named "the bTS02618Aa gene", encoding a (similar but different) protein with an insecticidal activity substantially similar to the BTS02618A protein.

Of course, the present invention is not limited to the particular preferred embodiments described herein as "alternative variants or forms." In fact, any other DNA sequences differing in their codon usage but encoding the same protein or a similar protein with substantially the same insecticidal activity, can be constructed by the person skilled in the art. In some prokaryotic and eucaryotic expression systems, for example, changing the codon usage to that of the host cell can increase gene expression (Bennetzen & Hall, 1982; Itakura, 1977). Moreover, since many Bt genes are known to have no bias towards eucaryotic codons, and to have very AT-rich genes it is sometimes beneficial to change the codon usage (Adang et al., 1985, Schnepf et al., 1985). To accomplish this codon usage tables which are available in the literature (Wada et al., 1990; Murray et al., 1989) and in the major DNA sequence databanks (e.g., EMBL at Heidelberg, Germany) are often referred to by the person skilled in the art. Accordingly, synthetic DNA sequences can be constructed so that the same or substantially the same proteins may be produced. See, for example, Cohen et al., 1973.

The term "substantially the same", when referring to a protein, is meant to include a protein that differs in some amino acids, or has some amino acids added (e.g., a fusion protein, see Vaeck et al., 1987) or deleted (e.g., N- or C-terminal truncation), while retaining the protein's insecticidal activity. It is generally known to those skilled in the art that general amino acid replacements in many parts of a polypeptide chain may be made without seriously modifying the activity of the polypeptide (Watson et al *Molecular Biology of the Gene* (1987) 226–227.

The term "functional parts of the BTS02618A toxin" as used herein means any part(s) or domain(s) of the toxin with a specific structure that can be transferred to another (Bt) protein for providing a new hybrid protein with at least one functional characteristic (e.g., the binding and/or toxicity characteristics) of the BTS02618A toxin (Ge et al., 1991). Such parts can form an essential feature of the hybrid Bt protein with the binding and/or toxicity characteristics of the BTS02618A protein. Such a hybrid protein can have an enlarged host range, an improved toxicity and/or can be used in a strategy to prevent insect resistance development (European Patent Publication ("EP") 408 403; Visser et al., 1993).

The "BTS02618Aa toxin", as used herein, refers to a new form of the BTS02618A toxin, differing in some amino acids from the native BTS02618A toxin. Indeed, the BTS02618A protoxin has been found to be digested by proteases into an about 69 kD protein and about 55 kD protein, the latter having substantially lower insecticidal activity. The longer the protease digestion, the more of the about 55 kD protein was formed. This 55 kD protein was found to be cleaved by digestion at the Arginine at amino acid position 164 shown in SEQ ID. No. 4. Thus, in the BTS02618Aa toxin, the Arginine at this position was replaced with a Lysine, the 43 N-terminal amino acids was replaced by amino acids Met-Ala, and the C-terminal end was truncated up to amino acid 666 (in SEQ ID. No. 4). Similar to other Bt toxins, the C-terminal end of the BTS02618Aa toxin can be further truncated to the minimum toxic fragment (up to amino acid 658 in SEQ ID. No. 4).

In another form of the BTS02618A protein, "the BTS02618Ab protein", this Arginine has been substituted with an Alanine. Both the BTS02618Aa/b proteins are less susceptible to proteases and still have substantially the same insecticidal activity. The part C-terminal from the toxic fragment of both the BTS02618Aa and BTS02618Ab protoxins is 100% identical to the C-terminal part of the BTS02618A protoxin.

The "bTS02618Aa gene" and the "bTS02618Ab gene", as used herein, refer to DNA sequences encoding respectively the BTS02618Aa and BTS02618Ab proteins. It is evident that several DNA sequences can be devised once the amino acid sequence of the BTS02618Aa and BTS02618Ab proteins are known. Such other DNA sequences include synthetic or semi-synthetic DNA sequences that have been changed in order to inactivate certain sites in the gene, e.g., by selectively inactivating certain cryptic regulatory or processing elements present in the native sequence as described in PCT publications WO 91/16432 and WO 93/09218, or by adapting the overall codon usage to that of a more related host organism, preferably that of the host organism, in which expression is desired.

Such a modification of the BTS02618A protein can also be achieved by deleting the Arginine at amino acid position 123, or by replacing this amino acid by another amino acid provided that the insecticidal activity of the new BTS02618A protein is not substantially changed. Other amino acids surrounding the protease cleavage site can also be altered such that the insecticidal activity is not substantially changed.

The new proteins can be tested in routine bio-assays to compare their toxicity with that of the native BTS02618A protein. The overall toxicity parameters of such proteins should be similar to those of the native proteins.

Due to the retention of their insecticidal activity, such new proteins are very useful for combatting important pest insects. Their improved resistance for protease activity makes them the toxins of choice for combatting insects, e.g., by expressing a DNA sequence encoding such proteins in a foreign host, such as bacteria or plants. Small modifications to a DNA sequence such as described above are routinely made by PCR-mediated mutagenesis (Ho et al.,1989, White et al., 1989).

The above variants show that indeed modifications can be made to the BTS02618A protein without causing any substantial changes to the insecticidal activity. Besides a deletion of up to 43 amino acids at the N-terminus, and a major deletion of C-terminal amino acids, also some internally located amino acids can be replaced by others while retaining substantially the same insecticidal activity of the BTS02618A toxin.

Similarly, the CryIB protoxin (Brizzard & Whiteley, 1988), and a naturally occurring variant thereof (EP publication 408 403) has been found to be cleaved into an about 69 kD toxin and a smaller about 55 kD toxin by protease activity. Also for this toxin, modification of the Arginine at amino acid positions 144 and 146 (relative to the start codon) in the sequence of Brizzard & Whiteley (1988) or the sequence of EP 408 403 can increase the stability of the protein in the insect gut. Indeed, prolonged protease treatment of the CryIB protoxin, either obtained from Bt strain 4412 or expressed in *E. coli*, resulted in an about 55 kD protein with an N-terminal end starting at amino acid position 145 (Thr-Arg-Ser-Val-Leu-) and another about 55 kD protein starting at position 147 (Ser-Val-Leu-Tyr-Thr-). Modifying the Arginine amino acids at positions 144 and 146 leads to a more stable toxin form, which is still toxic. This modification can be incorporated into a natural or synthetic DNA sequence encoding. the CryIB protein or variants thereof such as the Bt14 toxin in EP 358 557, by techniques well known in the art, so that a more stable CryIB protein is produced. Such a CryIB protein can be used together with the BTS02618A or BTS02618Aa protein and the CryIAb protein in combatting Lepidopteran insects, particularly *Ostrinia nubilalis*, by expressing DNA sequences encoding these proteins in a host cell, particularly a plant cell. So the modification of one or more amino acids is useful in other Bt proteins, particularly anti-Lepidoptera Bt proteins, that are also further cleaved by proteases.

Furthermore, the 5 to 10 Kb fragments, prepared from total DNA of the BTS02617A or BTS02618A or BTS02654B or BTS02652E strain, can be ligated in suitable expression vectors and transformed in *E. coli*, and the clones can then be screened by conventional colony immunoprobing methods (French et al., 1986) for expression of the toxin with monoclonal or polyclonal antibodies raised against the BTS02618A toxin.

Also, the 5 to 10 Kb fragments, prepared from total DNA of the BTS02617A or BTS02618A or BTS02654B or BTS02652E strain, can be ligated in suitable Bt shuttle vectors (Lereclus et al., 1992) and transformed in a crystal minus Bt-mutant. The clones are then screened for production of crystals (detected by microscopy) or crystal proteins (detected by SDS-PAGE).

The so-identified bTS02618A gene was sequenced in a conventional manner (Maxam and Gilbert, 1980) to obtain the DNA sequence. Hybridization in Southern blots and sequence comparison indicated that this gene is different from previously described genes encoding protoxins and toxins with activity against Lepidoptera (Höfte and Whiteley, 1989).

An insecticidally effective part of the bTS02618A gene, encoding an insecticidally effective portion of its protoxin, and a truncated part of the gene, encoding just its toxin, can be made in a conventional manner after sequence analysis of the gene. The amino acid sequence of the BTS02618A protoxin and toxin was determined from the DNA sequence of the bTS02618A gene and the truncated bTS02618A gene. By "an insecticidally effective part" or "a part" of the bTS02618A gene is meant a DNA sequence encoding a polypeptide which has fewer amino acids than the BTS02618A protoxin but which is still toxic to Lepidoptera.

In order to express all or an insecticidally effective part of the bTS02618A gene or an equivalent gene in *E. coli*, in other Bt strains and in plants, suitable restriction sites can be introduced, flanking each gene or gene part. This can be done by site-directed mutagenesis, using well-known procedures (Stanssens et al., 1989; White et al., 1989). In order to obtain improved expression in plants, it may be preferred to modify the codon usage of the bTS02618A gene or insecticidally effective bTS02618A gene part to form an equivalent, modified or artificial gene or gene part in accordance with PCT publications WO 91/16432 and WO 93/09218; EP 0,358,962 and EP 0,359,472. For obtaining enhanced expression in monocot plants such as corn, a monocot intron also can be added to the bTS02618A chimeric gene, and the DNA sequence of the bTS02618A gene part can be further changed in a translationally neutral manner, to modify possibly inhibiting DNA sequences present in the gene part by means of site-directed intron insertion and/or by introducing changes to the codon usage, e.g., adapting the codon usage to that most preferred by the specific plant (Murray et al., 1989) without changing significantly the encoded amino acid sequence.

Preferred examples of modified bTS02618A genes are shown in SEQ ID. Nos. 6 and 8, illustrating DNA sequences encoding the BTS02618A toxin and a variant thereof. These DNA sequences have an overall modified codon usage, which has been adapted to that of plants, particularly monocots such as corn. The DNA of SEQ ID. No. 6 encodes exactly the same toxin as the native bTS02618A gene, but yields higher expression levels in plants, particularly monocots such as corn, due to the adaptation of its codon usage to that of the plant host cells.

Furthermore, the BTS02618Aa toxin was found to bind to a receptor different from the CryIAb toxin receptor population in *Ostrinia nubilalis* gut membranes. This indicates that the BTS02618A toxin has a unique receptor in its susceptible insects. The broad spectrum, the binding to a different receptor and the low homology with other Bt toxins indicates that the BTS02618A toxin represents a new class of Bt toxins. Since the BTS02618A toxin apparently recognizes a different target site, it can prove to be especially useful for preventing the development of insect resistance, or for combatting insects resistant to other Bt toxins. Particularly the combined expression of the bTS02618A gene with other Bt genes encoding non-competitively binding toxins (as described in EP 408 403) in one host is interesting for preventing resistance development, preferably the combined expression of CryIAb and BTS02618A proteins.

Because of the broad spectrum of susceptible pest insects, the BTS02618A toxin and its variants are extremely useful for transforming plants, e.g., monocots such as corn and vegetables such as Brassicas, to protect these plants from insect damage.

The insecticidally effective bTS02618A gene part or its equivalent, preferably the bTS02618A chimeric gene, encoding an insecticidally effective portion of the BTS02618A protoxin, can be stably inserted in a conventional manner into the nuclear genome of a single plant cell, and the so-transformed plant cell can be used in a conventional manner to produce a transformed plant that is insect-resistant. In this regard, a disarmed Ti-plasmid, containing the insecticidally effective bTS02618A gene part, in *Agrobacterium tumefaciens* can be used to transform the plant cell, and thereafter, a transformed plant can be regenerated from the transformed plant cell using the procedures described, for example, in EP 0,116,718, EP 0,270,822, PCT publication WO 84/02,913 and European Patent Application ("EPA") 87/400,544.0 (which are also incorporated herein by reference), and in Gould et al. (1991). Preferred Ti-plasmid vectors each contain the insecticidally effective bTS02618A gene part between the border sequences, or at least located to the left of the right border sequence, of the T-DNA of the Ti-plasmid. Of course, other types of vectors can be used to transform the plant cell, using procedures such as direct gene transfer (as described, for example in EP 0,233,247), pollen mediated transformation (as described, for example in EP 0,270,356, PCT publication WO 85/01856, and U.S. Pat. No. 4,684,611), plant RNA virus-mediated transformation (as described, for example in EP 0,067,553 and U.S. Pat. No. 4,407,956), liposome-mediated transformation (as described, for example in U.S. Pat. No. 4,536,475), and other methods such as the recently described methods for transforming certain lines of corn (Fromm et al., 1990; Gordon-Kamm et al., 1990) and rice (Shimamoto et al., 1989; Datta et al., 1990) and the recently described method for transforming monocots generally (PCT publication WO 92/09696).

The resulting transformed plant can be used in a conventional plant breeding scheme to produce more transformed plants with the same characteristics or to introduce the insecticidally effective bTS02618A gene part in other varieties of the same or related plant species. Seeds, which are obtained from the transformed plants, contain the insecticidally effective bTS02618A gene part as a stable genomic insert. Cells of the transformed plant can be cultured in a conventional manner to produce the insecticidally effective portion of the BTS02618A protoxin, preferably the BTS02618A toxin, which can be recovered for use in conventional insecticide compositions against Lepidoptera (U.S. patent application Ser. No. 821,582; EPA 86/300291.1.).

The insecticidally effective bTS02618A gene part, preferably the truncated bTS02618A gene, is inserted in a plant cell genome so that the inserted gene is downstream (i.e., 3') of, and under the control of, a promoter which can direct the expression of the gene part in the plant cell. This is preferably accomplished by inserting the bTS02618A chimeric gene in the plant cell genome. Preferred promoters include: the strong constitutive 35S promoters (the "35S promoters") of the cauliflower mosaic virus of isolates CM 1841 (Gardner et al., 1981), CabbB-S (Franck et al., 1980) and CabbB-JI (Hull and Howell, 1987); and the TR1' promoter and the TR2' promoter (the "TR1' promoter" and "TR2' promoter", respectively) which drive the expression of the 1' and 2' genes, respectively, of the T-DNA (Velten et al., 1984). Alternatively, a promoter can be utilized which is not constitutive but rather is specific for one or more tissues or organs of the plant (e.g., leaves and/or roots) whereby the inserted bTS02618A gene part is expressed only in cells of the specific tissue(s) or organ(s). For example, the insecticidally effective bTS02618A gene part could be selectively expressed in the leaves of a plant (e.g., corn, cotton) by placing the insecticidally effective gene part under the control of a light-inducible promoter such as the promoter of the ribulose-1,5-bisphosphate carboxylase small subunit gene of the plant itself or of another plant such as pea as disclosed in U.S. patent application 821,582 and EPA 86/300,291.1. Another alternative is to use a promoter whose expression is inducible (e.g., by temperature or chemical factors).

The insecticidally effective bTS02618A gene part is inserted in the plant genome so that the inserted gene part is upstream (i.e., 5') of suitable 3' end transcription regulation signals (i.e., transcript formation and polyadenylation signals). This is preferably accomplished by inserting the bTS02618A chimeric gene in the plant cell genome. Preferred polyadenylation and transcript formation signals include those of the octopine synthase gene (Gielen et al., 1984) and the T-DNA gene 7 (Velten and Schell, 1985), which act as 3'-untranslated DNA sequences in transformed plant cells.

The insecticidally effective bTS02618A gene part can optionally be inserted in the plant genome as a hybrid gene (EPA 86/300,291.1; Vaeck et al., 1987) under the control of the same promoter as a selectable marker gene, such as the neo gene (EP 0,242,236) encoding kanamycin resistance, so that the plant expresses a fusion protein.

All or part of the bTS02618A gene, encoding an anti-lepidopteran protein, can also be used to transform other bacteria, such as a B. thuringiensis which has insecticidal activity against Lepidoptera or Coleoptera. Thereby, a transformed Bt strain can be produced which is useful for combatting a wide spectrum of lepidopteran and coleopteran insect pests or for combatting additional lepidopteran insect pests. Transformation of bacteria with all or part of the bTS02618A gene, incorporated in a suitable cloning vehicle, can be carried out in a conventional manner, preferably using conventional electroporation techniques as described in Mahillon et al. (1989) and in PCT Patent publication WO 90/06999.

Alternatively, mutants of the BTS02618A, BTS02617A, BTS02654B and BTS02652E strains can be obtained by treating these strains with mutagenic agents such as nitrosoguanidine or with UV light; techniques which are well known to those skilled in the art. Also, asporogenous mutants can be obtained by treatment with ethylmethane sulfonate. Such mutants can be screened for improved characteristics (such as suitability for large-scale fermentation and the like), while retaining substantially the same insecticidal activity.

The BTS02617A, BTS02618A, BTS02654B or BTS02652E strain also can be transformed with all or an insecticidally effective part of one or more foreign Bt genes such as: the bt18 gene (EP 0,358,557) or another Bt gene coding for an anti-Lepidoptera protein; and the bt109P gene (PCT publication WO 91/16433), coding for an anti-Coleoptera protein. Thereby, a transformed Bt strain can be produced which is useful for combatting an even greater variety of insect pests (e.g., Coleoptera and/or additional Lepidoptera).

Transformation of the BTS02617A, BTS02618A, BTS02654B or BTS02652E strain with all or part of a foreign Bt gene, incorporated in a conventional cloning vector, can be carried out in a well known manner, preferably using conventional electroporation techniques (Chassy et al., 1988) or other methods, e.g., as described by Lereclus et al. (1992).

Each of the BTS02617A, BTS02618A, BTS02654B or BTS02652E strains can be fermented by conventional methods (Dulmage, 1981; Bernhard and Utz, 1993) to provide high yields of cells. Under appropriate conditions which are well understood (Dulmage, 1981), the BTS02617A, BTS02618A, BTS02654B and BTS02652E strains each sporulate to produce crystal proteins containing the BTS02168A protoxin in high yields.

An insecticidal, particularly anti-lepidopteran, composition of this invention can be formulated in a conventional manner using the BTS02617A, BTS02618A, BTS02654B or BTS02652E strain or preferably their respective crystals, crystal proteins or the BTS02168A protoxin, toxin or insecticidally effective protoxin portion as an active ingredient, together with suitable carriers, diluents, emulsifiers and/or dispersants (e.g., as described by Bernhard and Utz, 1993). This insecticide composition can be formulated as a wettable powder, pellets, granules or dust or as a liquid formulation with aqueous or non-aqueous solvents as a foam, gel, suspension, concentrate, etc. The concentration of the BTS02617A, BTS02618A, BTS02654B or BTS02652E strain, crystals, crystal proteins, or the BTS02618A protoxin, toxin or insecticidally effective protoxin portions in such a composition will depend upon the nature of the formulation and its intended mode of use. Generally, an insecticide composition of this invention can be used to protect a field for 2 to 4 weeks against Lepidoptera with each application of the composition. For more extended protection (e.g., for a whole growing season), additional amounts of the composition should be applied periodically.

A method for controlling insects, particularly Lepidoptera, in accordance with this invention preferably comprises applying (e.g., spraying), to a locus (area) to be protected, an insecticidal amount of the BTS02617A, BTS02618A, BTS02654B or BTS02652E strain, spores, crystals, crystal proteins or the BTS02168A protoxin, toxin or insecticidally effective protoxin portions, preferably the BTS2168A toxin. The locus to be protected can include, for example, the habitat of the insect pests or growing vegetation or an area where vegetation is to be grown.

To obtain the BTS02618A protoxin or toxin, cells of the BTS02617A, BTS02618A, BTS02654B or BTS02652E strain can be grown in a conventional manner on a suitable culture medium and then lysed using conventional means such as enzymatic degradation or detergents or the like. The protoxin can then be separated and purified by standard techniques such as chromatography, extraction, electrophoresis, or the like. The toxin can then be obtained by trypsin digestion of the protoxin.

The BTS02617A, BTS02618A, BTS02654B or BTS02652E cells can also be harvested and then applied intact, either alive or dead, preferably dried, to the locus to be protected. In this regard, it is preferred that a purified BTS02617A, BTS02618A, BTS02654B or BTS02652E strain (either alive or dead) be used, particularly a cell mass that is 90.0 to 99.9% of the BTS02617A, BTS02618A, BTS02654B or BTS02652E strain.

The BTS02617A, BTS02618A, BTS02654B, or BTS02652E cells, crystals or crystal proteins or the BTS02618A protoxin, toxin, or insecticidally effective protoxin portion can be formulated in an insecticidal composition in a variety of ways, using any number of conventional additives, wet or dry, depending upon the particular use. Additives can include wetting agents, detergents, stabilizers, adhering agents, spreading agents and extenders. Examples of such a composition include pastes, dusting powders, wettable powders, granules, baits and aerosol sprays. Other Bt cells, crystals, crystal proteins, protoxins, toxins, and insecticidally effective protoxin portions and other insecticides, as well as fungicides, biocides, herbicides and fertilizers, can be employed along with the BTS02617A, BTS02618A, BTS02654B or BTS02652E cells, crystals or crystal proteins or the BTS02618A protoxin, toxin or insecticidally effective protoxin portions to provide additional advantages or benefits. Such an insecticidal composition can be prepared in a conventional manner, and the amount of the BTS02617A, BTS02618A, BTS02654B or BTS02652E cells, crystals or crystal proteins or the BTS02618A protoxin, toxin or insecticidally effective protoxin portion employed depends upon a variety of factors, such as the insect pest targeted, the composition used, the type of area to which the composition is to be applied, and the prevailing weather conditions. Generally, the concentration of the BTS02618A protoxin, insecticidally effective protoxin portions or toxin will be at least about 0.1% by weight of the formulation to about 100% by weight of the formulation, more often from about 0.15% to about 0.8% by weight of the formulation.

In practice, some insects can be fed the BTS02618A protoxin, toxin, insecticidally effective protoxin portion or mixtures thereof in the protected area, that is in the area where such protoxin, toxin and/or insecticidally effective protoxin portion has been applied. Alternatively, some insects can be fed intact and alive cells of the BTS02617A, BTS02618A, BTS02654B or BTS02652E strain or transformants thereof, so that the insects ingest some of the strain's protoxin and suffer death or damage.

For the purpose of combatting insects by contacting them with the BTS02618A protein, e.g., in the form of transformed plants or insecticidal formulations and the like, any of the above described variants of the BTS02618A protein with substantially the same insecticidal activity can be used, preferably the BTS02618Aa and BTS02618Ab proteins. Furthermore, any of the above-described methods for transforming plants and bacteria can also be utilized to combat insects with the BTS02618Aa or BTS02618Ab proteins or other more protease resistant protein variants of the BTS02618A protein in lieu of the native BTS02618A protein.

The following Examples illustrate the invention. The sequence listing referred to in the Examples is as follows:

Sequence Listing

SEQ ID No. 1—Nucleotide sequence of the DNA probe used to isolate the bTS02618A gene. This probe is derived from part of the cryIG DNA sequence and is complementary to nucleotides 2732–2750 of the DNA sequence described by Smulevitch et al. (1991).

SEQ ID No. 2—The 5' partial nucleotide sequence of the bTS02618A gene, comprising the presumptive translation initiation codon at nucleotide position 195–197.

SEQ ID No. 3—The 3' partial nucleotide sequence of the bTS02618A gene (N: unknown nucleotide), comprising the presumptive translational stop codon at nucleotide position 1146–1148.

SEQ ID No. 4—The nucleotide sequence of the bTS02618A gene and the translated amino acid sequence of the BTS02618A protoxin. The open reading frame of the protoxin reaches from nucleotide 668 to nucleotide 4141. The translation initiation codon is at nucleotide position 668–670, the translation stop codon is at nucleotide position 4139–4141.

SEQ ID. No. 5—The amino acid sequence of the BTS02618A protein. The sequence of the about 69 kD BTS02618A toxin stretches from amino acid 44 to amino acid 658.

SEQ ID. No. 6—The nucleotide sequence of a modified truncated bTS02618A gene, and the translated amino acid sequence of the BTS02618A toxin.

SEQ ID. No. 7—The translated amino acid sequence of the modified bTS02618A toxin gene. Although only the toxin part is shown here, the full length protein is 100% identical in amino acid sequence to the BTS02618A protein (SEQ ID. No.5).

SEQ ID. No. 8—The nucleotide sequence of the modified bTS02618Aa toxin gene, and the translated amino acid sequence of the BTS02618Aa toxin. Besides N- and C-terminal amino acid deletions and the addition of an Alanine codon after the N-terminal Methionine codon, the BTS02618Aa toxin only differs from the BTS02618A toxin in amino acid number 123 (Arg codon has been changed into a Lys codon).

SEQ ID. No. 913 The amino acid sequence of the BTS02618Aa toxin. The BTS02618Aa protoxin is 100% identical to the BTS02618A protoxin in its part C-terminal from the toxin fragment.

Unless otherwise stated in the Examples, all procedures for making and manipulating recombinant DNA are carried out by the standardized procedures described in Sambrook et al., *Molecular Cloning—A Laboratory Manual, Second Ed.*, Cold Spring Harbor Laboratory Press, NY (1989).

Example 1

Characterization of the BTS02617A. BTS02618A BTS02654B and BTS02652E Strains

The BTS02617A, the BTS02618A and the BTS02654B strain were isolated from grain dust sampled in Cadlan, province of Bicol, The Philippines and were deposited at the BCCM-LMG on Jul. 2, 1992 under accession Nos. LMG P-12592, LMG P-12593 and LMG P-12594, respectively. Strain BTS02652E was also isolated from Philippine grain dust, and was deposited at the BCCM-LMG on Mar., 1, 1993 under accession No. LMG P-13493.

Each strain can be cultivated on conventional standard media, preferably $T_3$ medium (tryptone 3 g/l, tryptose 2 g/l, yeast extract 1.5 g/l, 5 mg $MnCl_2$, 0.05 M $Na_2PO_4$, pH 6.8 and 1.5% agar), preferably at 28° C. For long term storage, it is preferred to mix an equal volume of a spore-crystal suspension with an equal volume of 50% glycerol and store this at −70° C. or lyophilize a spore-crystal suspension. For sporulation, growth on $T_3$ medium is preferred for 48 hours at 28° C., followed by storage at 4° C. During its vegetative phase, each of the strains can also grow under facultative anaerobic conditions, but sporulation only occurs under aerobic conditions.

Sterilization of each strain occurs by autoclave treatment at 120° C. (1 bar pressure) for 20 minutes. Such treatment totally inactivates the spores and the BTS02617A, BTS02618A, BTS02654B, and BTS02652E protoxins. UV radiation (254 nm) also inactivates the spores.

After cultivating on Nutrient Agar ("NA", Difco Laboratories, Detroit, Mich., USA) for one day, colonies of each of the BTS02617A, BTS02618A, BTS02654B and BTS02652E strains form opaque white colonies with irregular edges. Cells of each strain (Gram positive rods of 1.7–2.4×5.6–7.7 µm) sporulate after 48 hrs cultivation at 28° C. on $T_3$ agar. The crystal proteins produced during sporulation are packaged in crystals of the BTS02617A, BTS02618A, BTS02654B, and BTS02652E strains. Quite remarkably, the crystal remains attached to the spore after sporulation.

The Bt serotype of the BTS02617A, BTS02618A, BTS02654B and BTS02652E strains was determined to be serotype tolworthi H9 of all these strains which was determined by conventional serotyping methods as conducted by the WHO Collaborating Center for Entomopathogenic Bacillus.

Example 2

Insecticidal Activity of the BTS02617A, BTS02618A. BTS02654B and BTS02652E Strains, the BTS02618A Protoxin and the BTS02618Aa and BTS02618Ab Toxins or Protoxins Against Noctuidae spp., Gelechiidae spp., Yponomeutidae spp. and Pyralidae spp Toxicity assays were performed on neonate larvae (for *Plutella xylostella*, third instar larvae were used) fed on an artificial diet layered with spore-crystal mixtures from one of the BTS02617A, BTS02618A, BTS02654B and BTS02652E strains or the BTS02618A protoxin or toxin or the BTS02618Aa and BTS02618Ab toxins or protoxins. The artificial diet was dispensed in wells of Costar 24-well plates. Formaldehyde was omitted from the diet. 50 µl of a sample dilution was applied on the surface of the diet and dried in a laminar air flow. For $LC_{50}$ assays, the dilutions were made in a PBS-BSA buffer, and five dilutions were applied. Two larvae were placed in each well and 24 larvae were used per sample dilution. Dead and living *M. brassica, S. frugiperda, H. virescens, O. nubilalis, Plutella xylostella* and *S. exigua* larvae were counted on the fifth day, and dead and living *A. ipsilon, A. segetum* and *S. littoralis* larvae were counted on the sixth day. The $LC_{50}$ and $LC_{95}$ values (the concentrations required to kill respectively 50% or 95% of the insects tested, expressed in number of spore-crystals/cm² or ng (pro) toxin/cm²) were calculated using Probit-analysis (Finney, 1971), and the results are set forth below.

The potato moth, *Phthorimaea operculella*, was tested by the following assay: disks, cut from potato tubers, were dipped in solutions of varying concentrations of BTS0216Aa protein. Three of such disks, which were allowed to dry, were placed in a tray with 20 Phthorimaea larvae. Mortality was recorded after 4 to 5 days for each concentration applied.

*Spodoptera littoralis*

| Experiment/Strain | $LC_{50}$[a] | $LC_{95}$[a] | $FL_{min-max}$[b] | Slope |
|---|---|---|---|---|
| Experiment 1 | | | | |
| BTS02618A | 2.4 | 7.7 | 1.5–3.4 | 3.2 |
| HD127[c] | 2.5 | 168 | 1.2–7.4 | 1.0 |

-continued

| Experiment/Strain | $LC_{50}$[a] | $LC_{95}$[a] | $FL_{min-max}$[b] | Slope |
|---|---|---|---|---|
| Experiment 2 | | | | |
| BTS02618A | 1.1 | 4 | 0.8–1.6 | 3.0 |
| HD127 | 21.2 | 133.7 | 14.4–31.9 | 2.0 |

[a]10⁵ spore-crystals per cm²
[b]95% fiducial limits of $LC_{50}$ values
[c]from the Howard Dulmage collection, housed at the Northern Region Research Center, 1815 North University, Peoria, Ill, USA. The curator is Dr. L. Nakamura.

Experiments with purified BTS02618A protoxin also show a significant toxicity of this protoxin against *S. littoralis* larvae.

*Spodoptera exigua*

1. Crystal/spore Mixtures

| Experiment/Strain | $LC_{50}$[a] | $LC_{95}$[a] | $FL_{min-max}$[b] | Slope |
|---|---|---|---|---|
| Experiment 1 | | | | |
| BTS02618A | 1.4 | 7.9 | 0.48–3.9 | 2.2 |
| HD127 | 8.2 | 163.5 | 5.1–15.7 | 1.3 |
| Experiment 2 | | | | |
| BTS02618A | 1.2 | 3.56 | 0.91–1.57 | 3.5 |
| BTS02617A | 0.79 | 2.12 | 0.61–1.03 | 3.81 |
| HD127 | 3.5 | 44.2 | 1.36–11.5* | 1.5 |
| Florbac | 4.1 | 53.9 | 1.5–17.0* | 1.47 |
| BTS00170U[c] | 5.1 | 46.5 | 1.83–24.4* | 1.71 |
| Experiment 3 | | | | |
| Javelin[d] | 23.12 | 195.7 | 14.6–56.7 | 1.77 |
| Experiment 4 | | | | |
| BTS02618A | 1.07 | 2.91 | 0.83–1.39 | 3.8 |
| BTS02617A | 0.87 | 4.7 | 0.59–1.21 | 2.22 |
| HD127 | 4.7 | 56.9 | 1.85–18.7* | 1.52 |
| Florbac[e] | 2.53 | 48.1 | 0.79–6.71* | 1.29 |
| BTS00170U | 1.94 | 56.3 | 0.55–5.4* | 1.12 |

[a]10⁵ spore-crystals per cm²
[b]95% fiducial limits of $LC_{50}$ values, values marked with * are 90% fiducial limits of $LC_{50}$ values
[c]PCT patent publication WO 90/06999
[d]strain isolated from Javelin ® (Sandoz, Lichtstrasse, Basel, Switzerland)
[e]strain from Florbac ® (Novo Nordisk, Novo Alle, Bagsværd, Denmark)

2. Toxin/protoxin Assays

| ICP | | $LC_{50}$[a] | $LC_{95}$[a] | $FL_{min-max}$[b] | Slope |
|---|---|---|---|---|---|
| BTS02618A | Protoxin | 26.6 | 100.6 | 20.9–33.9 | 2.8 |
| CryIC | Toxin | 68.9 | 313.2 | 50.5–94.1 | 2.5 |
| CryID | Toxin | 118.6 | 870.6 | 82.7–170.0 | 1.9 |

[a]ng/cm²
[b]95% fiducial limits of $LC_{50}$ values

*Mamestra brassica*

1. Crystal/spore Mixtures

| Experiment/Strain | $LC_{50}$[a] | $LC_{95}$[a] | $FL_{min-max}$[b] | Slope |
|---|---|---|---|---|
| HD127 | 37.8 | 297.6 | 17.8–91.1 | 1.8 |
| BTS02618A | 8.6 | 59.6 | 6.0–12.2 | 1.9 |
| BTS02617A | 5.2 | 25.8 | 3.7–7.1 | 2.4 |

-continued

| Experiment/Strain | $LC_{50}$[a] | $LC_{95}$[a] | $FL_{min-max}$[b] | Slope |
|---|---|---|---|---|
| BTS02652E | 12.9 | 44.2 | 9.7–17.2 | 3.0 |
| BTS02654B | 14.2 | 60.5 | 10.8–19.9 | 2.6 |

[a]$10^5$ spore-crystals per $cm^2$
[b]95% fiducial limits of $LC_{50}$ values

2. Protoxin Assays

| ICP | | $LC_{50}$[a] | $LC_{95}$[a] | $FL_{min-max}$[b] | Slope |
|---|---|---|---|---|---|
| BTS02618A | Protoxin | 25.3 | 125.1 | 19.3–33.2 | 2.4 |
| CryIC | Protoxin | 22.0 | 62.9 | 16.3–29.6 | 3.6 |
| CryIA (b) | Protoxin | 162.4 | 7169 | 93.2–283.1 | 1.0 |

[a]$ng/cm^2$
[b]95% fiducial limits of $LC_{50}$ values

*Agrotis ipsilon*

1. Crystal/spore Mixtures

| Strain | mortality[a] | genes[b] |
|---|---|---|
| Btgall.[c] | 1/20 | cryIF, cryIG, cryII, 81k |
| HD127[d] | 2/20 | cryIAa, cryIAb, cryIC, cryID, cryII, 81k |
| BTS02618A | 16/20[e] | cryIAb, cryII, bTS02618A |
| Buffer | 1/20 | none |

[a]number of 1st instar larvae killed after 6 days ($10^7$ sporecrystals per $cm^2$)
[b]genes known to be present in these strains
[c]Btgall. as described by Smulevitch et al (1991)
[d]HD127 is available at the Howard Dulmage Collection (NRRC, see above)
[e]surviving larvae show severe growth-inhibition

| STRAIN | $LC_{50}$[a] | $LC_{95}$[a] | $FL_{min-max}$[b] | Slope |
|---|---|---|---|---|
| BTS02618A | 84.4 | 207.9 | 65.6–109.6 | 4.2 |
| HD127 | >250 | | | |
| BTS02618A | 53.4 | 261.0 | 27.7–112.3 | 2.4 |

[a]$10^6$ spores/$cm^2$
[b]95% fiducial limits of $LC_{50}$ values

2. Toxin/protoxin Assay

| ICP | | $LC_{50}$[a] | $LC_{95}$[a] | $FL_{min-max}$[b] | Slope |
|---|---|---|---|---|---|
| CryIAc | Toxin | >1350 | | | |
| BTS02618A | Protoxin | 212.2 | 1973 | 168.1–267.0 | 107 |

[a]$ng/cm^2$
[b]95% fiducial limits of $LC_{50}$ values

Since MacIntosh et al. (1990) described some activity of the CryIAc toxin towards *A. ipsilon*, purified CryIAc toxin was tested on this insect for comparison but did not cause any significant mortality of *A. ipsilon*.

Heliothis virescens
1. Crystal/spore Mixture

| Experiment/Strain | $LC_{50}$[a] | $LC_{95}$[a] | $FL_{min-max}$[b] | Slope |
|---|---|---|---|---|
| BTS02617A | 1.69 | 14.99 | 0.67–2.89 | 1.73 |
| BTS02618A | 2.71 | 25.4 | 0.88–6.99 | 1.69 |
| BTS00170U[c] | 15.1 | 398.7 | 8.3–41.2 | 1.15 |
| Dipel[d] | 2.99 | 14.11 | 1.25–7.76 | 2.45 |

[a]$10^3$ spore-crystals per $cm^2$
[b]95% fiducial limits of $LC_{50}$ values
[c]PCT patent publication WO 90/06999
[d]strain isolated from Dipel ™ (Abbott Laboratories, North Chicago, Ill., USA)

2.Toxin/protoxin Assay

| ICP | | $LC_{50}$[a] | $FL_{min-max}$[b] | $LC_{95}$[a] | Slope |
|---|---|---|---|---|---|
| BTS02618A | Protoxin | 31.6 | 20–50 | 182.7 | 2.1 |
| CryIAb | Toxin | 7.2 | 4.9–10.5 | 169.1 | 1.2 |

[a]$ng/cm^2$
[b]95% fiducial limits of $LC_{50}$ values

*Ostrinia nubilalis*
1. Crystal/spore Mixtures

| Experiment/Strain | $LC_{50}$[a] | $LC_{95}$[a] | $FL_{min-max}$[b] | Slope |
|---|---|---|---|---|
| BTS02617A | 4.92 | 12.49 | 2.45–6.81 | 4.0 |
| BTS02618A | 6.17 | 39.7 | 2.93–9.74 | 2.0 |
| Dipel[c] | >30 | | | |

[a]$10^5$ spore-crystals per $cm^2$
[b]95% fiducial limits of $LC_{50}$ values
[c]strain isolated from Dipel ™ (Abbott Laboratories)

2. Purified Protoxin Assay

| ICP | | 100% Mortality[a] |
|---|---|---|
| CryIAb | Toxin | 1350 |
| CryIB | Toxin | 1350 |
| BTS02618A | Protoxin | 100 |

[a]concentration at which 100% mortality was observed (in $ng/cm^2$)

The purified BTS02618A protoxin also showed a significant toxicity to *Ostrinia nubilalis* larvae, as compared with the CryI toxins that are most active against Ostrinia.

*Plutella xylostella*

*Plutella xylostella* larvae also showed significant mortality after application of purified BTS02618A toxin to their artificial diet in several experiments.

*Spodoptera frugiperda*

Crystal/spore mixtures of a bTS02618A gene-transformed crystal-minus Bt strain (Mahillon et al., 1989) were also found to significantly inhibit larval growth of *S. frugiperda* larvae in insect feeding trials.

*Agrotis segetum*

The cutworm *Agrotis segetum* was also found to be susceptible to the BTS02618Aa toxin. This variant of the BTS02618A protein killed 50% of the Agrotis larvae at a concentration of BTS02618Aa toxin of 980 $ng/cm^2$ (=$LC_{50}$). In comparative assays, all other CryI toxins tested (CryIAb, CryIAc, CryIAa, CryIB, CryIC, CryID, CryIE (Hofte & Whiteley 1989; EP 358 557)) were found to have an $LC_{50}$ of more than 15.000 ng/cm² for this insect. *Agrotis segetum* is an important pest insect on various crops.

*Phthorimaea operculella*.

Also the potato tubermoth, *Phthorimaea operculella*, was found to be susceptible to the BTS02618Aa toxin. Larvae which ingested the BTS02618A toxin showed a significantly higher mortality rate than control larvae.

Furthermore, the BTS02618Aa toxin was tested on several insects and was found to have substantially the same insecticidal activity as the BTS02618A protein. Indeed, bio-assays were conducted with *Heliothis virescens*, *Mamestra brassicae*, *Ostrinia nubilalis*, *Spodoptera exigua* and *Spodoptera littoralis*, and these showed only minor differences in $LC_{50}$ values when compared to the BTS02618A protein. This shows that the new BTS02618Aa toxin does not differ substantially in insecticidal activity from the native form.

Also, an Alanine mutant of the BTS02618A toxin and protoxin, the BTS02618Ab toxin and the BTS02618Ab protoxin, were tested on *Ostrinia nubilalis* and were found to be substantially as toxic as the BTS02618Aa toxin or protoxin.

At the same time, the BTS02618Aa toxin was found to be non-toxic to the tested Coleopteran insects: *Leptinotarsa decemlineata* and *Diabrotica undecimpunctata howardi* were not affected by the BTS02618Aa toxin. These insects were tested in diet application assays well known in the art. See, for example, Rupar et al., 1991.

In conclusion, the strains of this invention and the BTS02618A protein of this invention and its variants have a strong insecticidal activity against a broad range of insects that are not susceptible to any single currently available Bt protein and have an activity against at least three Spodoptera spp. and against other Noctuidae, such as *A. ipsilon, A. segetum, M. brassica* and *H. virescens*, as well as against Pyralidae, such as *O. nubilalis*, Gelechiidae such as *P. operculella* and Yponomeutidae such as *Plutella xylostella*. These results are summarized and compared with results for other CryI genes (Van Frankenhuyzen, 1993) in Table 1 which shows the unique range of insects susceptible to the BTS02618A protein.

The same spectrum applies for the BTS02618Aa and BTS02618Ab toxins. So these new toxins can also be used for combatting insects, and they have the added advantage that they are more stable, due to their lower susceptibility to protease activity, since almost no about 55 kD protein is formed.

Example 3

Identification of the bTS02618A Gene

The bTS02618A gene was identified in the BTS02618A strain by Southern blot analysis (FIG. 1) of AluI digested total DNA of the strain using, as a DNA probe, the DNA sequence of the cryIG gene (Gleave et al., 1992) of SEQ ID No. 1 and using standard hybridization conditions. Partial DNA sequences of the bTS02618A gene, showing its 5' and 3' end portions, are shown in SEQ ID Nos. 2 and 3, respectively, and the full DNA sequence of the bTS02618A gene and the full amino acid sequence of the BTS02618A protein are shown in SEQ ID No. 4.

The partial sequences of SEQ ID Nos. 2 and 3 allow the bTS02618A gene to be recognized in the BTS02617A, BTS02654B and BTS02652E strains and allow the construction of probes to identify and isolate the full gene sequence in these and other Bt strains. The translation initiation codon of the bTS02618A gene is identified at nucleotide position 195–197 in SEQ ID No. 2, corresponding to nucleotide position 668–670 in SEQ ID No. 4. The translation stop codon is identified at nucleotide position 1146–1148 in SEQ ID No. 3, corresponding to nucleotide position 4139–4141 in SEQ ID No. 4.

The bTS02618A gene was also identified in the BTS02617A, BTS02654B and BTS02652E strains by using the DNA sequence of SEQ ID No. 1 as a probe, as well as other DNA probes of conserved DNA fragments in cryI genes.

The full length bTS02618A gene was found to encode a 129.9 kD protoxin. A comparison of the amino acid sequence with other known CryI proteins showed that the C-terminal part (C-terminal of conserved sequence block 5) was homologous with CryIG (88%). The best homology for the N-terminal part (the toxin) was found with the CryIB toxin, but this was found to be less than 50% (homology is expressed as the number of perfect matches divided by the number of amino acids of the longest fragment).

The smallest insecticidal protein is believed to be a 69 kD (615 amino acids) protein stretching from amino acid number 44 to amino acid number 658 in SEQ ID No. 4. A smaller tryptic fragment of 55 kD (494 amino acids), stretching from amino acid number 165 to amino acid number 658 in SEQ ID No. 4, still has insecticidal activity towards *S. exigua*, but this activity is significantly reduced. Thus, a truncated bTS02618A gene or an equivalent truncated gene preferably encodes the 69 kD protein of the BTS02618A protoxin of SEQ ID No.4 as described above.

Example 4

Cloning and Expression of the bTS02618A Gene

In order to isolate the bTS02618A gene, total DNA from the BTS02618A strain was prepared and partially digested with Sau3A. The digested DNA was size fractionated on a sucrose gradient and fragments ranging from 7 Kb to 10 Kb were ligated to the BamH1-digested and BAP-treated cloning vector pUC19 (Yannisch-Perron et al., 1985). Recombinant *E.coli* clones containing the vector were then screened with the cryIG DNA probe of SEQ ID No. 1 which is described in Example 3, to identify clones containing the bTS02618A gene.

The so-identified DNA fragments were then sequenced according to Maxam and Gilbert (1980). Partial sequences of the bTS02618A gene are shown in SEQ ID Nos. 2 and 3, and a full sequence of the bTS02618A gene and the BTS02618A protein is shown in SEQ ID No. 4. Based on the DNA sequence analysis, the gene is cut with appropriate restriction enzymes to give the truncated bTS02618A gene encoding the BTS02618A toxin. Expression of the gene in *E.coli* was induced using standard procedures (Sambrook et al., 1989, supra).

The bTS02618A gene was also introduced by routine procedures into a crystal-minus Bt 1715 berliner strain and a Bt HD-1 kurstaki strain (the production strain of Dipel™ (Abbott Laboratories)) under the control of its own bacterial promoter, using an appropriate shuttle vector (Mahillon et al., 1988).

Spore-crystal mixtures of 2 transformants of Bt strain kurstaki HD-1 (containing the bTS02618A gene), the parental Bt kurstaki HD-1 strain, the wild-type BTS02618A strain, the Bt 1715 berliner crystal-minus strain and one transformant of Bt 1715 berliner crystal-minus (containing the bTS02618A gene) were bioassayed on beet armyworm (*Spodoptera exigua*). Bioassays were performed as described in Example 2. The transformed Bt 1715 berliner crystal-minus (containing bTS02618A) was highly toxic to *S. exigua* (100% mortality at $4\times10^4$ spore-crystals per square cm of diet agar) while the Bt 1715 berliner crystal-minus was not toxic. The Bt kurstaki HD-1 (bTS02618A) transformants were (on average) 22 times ($LC_{50}$-level) to 76 times ($LC_{95}$-level) as toxic as the parental HD-1 (Table 2).

Similarly, the BTS02618Aa protein or other variants of the BTS02618A protein can be transferred to and expressed in a Bt strain by any method available in the art (Baum et al., 1991; Gamel & Piot, 1992; Lecadet et al., 1992), provided the vector used is compatible with the Bt host strain, and is stably maintained in the bacterial host. It is known that plasmid vectors having replicon homology with the host strain are not suitable vectors (Gamel & Piot, 1992).

Example 5

Insertion of the bTS02618A Gene and the Truncated bTS02618A Gene in *E. coli* and Insertion of the Truncated bTS02618A Gene in Plants In order to express the bTS02618A gene and the truncated bTS02618A gene of Example 4 in *E. coli* and in plants, different gene cassettes are made in *E. coli* according to the procedure described in EPA 86/300291.1 and EPA 88/402115.5.

To allow significant expression in plants, cassettes containing a) the truncated gene or b) a hybrid gene that is a fusion of i) the truncated gene and ii) the neo gene are each: inserted between the T-DNA border sequences of intermediate plant expression vectors as described in EPA 86/300291.1; fused to transcript formation and polyadenylation signals in the plant expression vectors; placed under the control of the constitutive promoter from cauliflower mosaic virus driving the 35S3 transcript (Hull and Howell, 1987) or the 2' promoter from the TR-DNA of the octopine Ti-plasmid (Velten et al., 1984); and fused to 3' end transcript formation and polyadenylation signals of the octopine synthase gene (Gielen et al., 1984).

Using standard procedures (Deblaere et al., 1985), the intermediate plant expression vectors, containing the truncated bTS02618A gene, are transferred into the Agrobacterium strain C58C1Rif$^R$ (U.S. patent application 821,582; EPA 86/300,291.1) carrying the disarmed Ti-plasmid pGV2260 (Vaeck et al., 1987). Selection for spectinomycin resistance yields cointegrated plasmids, consisting of pGV2260 and the respective intermediate plant expression vectors. Each of these recombinant Agrobacterium strains is then used to transform different cotton plants so that the truncated bTS02618A gene is contained in, and expressed by, different plant cells.

Example 6

Expression of the Truncated bTS02618A Gene in Plants.

The insecticidal activity against Lepidoptera of the expression products of the truncated bTS02618A gene in leaves of transformed plants, generated from the transformed plant cells of Example 5, is evaluated by recording the growth rate and mortality of Agrotis and Spodoptera spp. larvae fed on these leaves. These results are compared with the growth rate of larvae fed leaves from untransformed plants. Toxicity assays against Agrotis and Spodoptera spp. are performed as described in EP 0,358,557, U.S. patent application 821,582 and EPA 86/300,291.1.

A significantly higher mortality rate is obtained among larvae fed on leaves of transformed plants containing the truncated bTS02618A gene and the truncated bTS02618A-neo hybrid gene than among larvae fed the leaves of untransformed plants. The transformed plants are also found to resist *Ostrinia nubilalis, Mamestra brassica, Heliothis virescens* and *Plutella xylostella* attack by their expression of the BTS02618A protein.

Needless to say, this invention is not limited to the BTS02617A strain (BCCM-LMG P-12592), the BTS02618A strain (BCCM-LMG P-12593), the BTS02654B strain (BCCM-LMG P-12594) and the BTS02652E (BCCM-LMG P-13493) strain. Rather, the invention also includes any mutant or variant of the BTS02617A, BTS02618A, BTS02654B, and BTS02652E strain which produces crystals, crystal proteins, protoxin or toxin having substantially the same properties, particularly anti-Lepidoptera properties, quite particularly anti-Noctuidae, anti-Yponomeutidae, anti-Gelechiidae and anti-Pyralidae properties, especially anti-Spodoptera, anti-Plutella, anti-Ostrinia, anti-Mamestra; anti-Heliothis, anti-Phthorimaea and anti-Agrotis properties, as the respective BTS02617A, BTS02618A, BTS02654B or BTS02652E crystals or crystal proteins, or the BTS02618A protoxin or toxin. This invention also includes the bTS02618A gene and any insecticidally effective parts thereof, like the truncated bTS02618A gene. In this regard, the term "bTS02618A gene" as used herein means the gene isolated from the BTS02617A, BTS02618A, BTS02654B or BTS02652E strain and hybridizing to the nucleotide sequence of SEQ ID No. 1 and any equivalent gene encoding a protoxin having substantially the same amino acid sequence and insecticidal activity as the BTS02618A protoxin and preferably containing the partial nucleotide sequences shown in SEQ ID Nos. 2 and 3, or the full sequence shown in SEQ ID No. 4.

This invention also is not limited to cotton plants transformed with the truncated bTS02618A gene. It includes any plant, such as tomato, tobacco, rapeseed, alfalfa, sunflower, lettuce, potato, corn, rice, soybean, Brassica species, sugar beet and other legumes and vegetables, transformed with an insecticidally effective part of the bTS02618A gene or an equivalent gene such as the bTS02618Aa gene.

Methods for transforming corn cells and regenerating transgenic plants have been described (D'Halluin et al., 1992; Fromm et al., 1990; Gould et al., 1991; Koziel et al., 1993; Omirulleh et al., 1993; Spencer et al., 1992; Klein et al., 1992; Walters et al., 1992). Vectors for transforming corn cells contain chimeric genes encoding a bTS02618A protein or variant thereof (e.g., BTS02618Aa), comprising suitable promoters such as derivatives of the 35S promoter or a promoter from a maize gene, preferably a constitutively expressed maize gene; and suitable 3' end formation sequences such as those of natural maize genes or those derived from the 35S, gene7 or octopine synthase genes (See, Detailed Description and Mogen et al 1990; Wu et al 1993). Increased expression may be obtained when an intron is introduced in the chimeric gene construct (e.g. a natural maize gene intron such as the AdhI intron (see Callis et al., 1987; Maas et al., 1991)), provided the intron is correctly spliced in the corn cells. Enhancer elements can also be provided in the promoter sequence (e.g., Omirulleh et al., 1993). Transgenic corn plants are grown on selective media by inclusion of well known selectable marker genes such as herbicide resistance genes or antibiotic resistance genes as chimeric genes in the transforming DNA. Transgenic corn plants are selected for their transformed phenotype by means of bio-assays on *Ostrinia nubilalis* larvae. These larvae quickly stop feeding on the bTS02618Aa-transformed corn and cause no major damage to the corn plants.

This invention is not limited to the use of *Agrobacterium tumefaciens* Ti-plasmids for transforming plant cells with an insecticidally effective bTS02618A gene part. Other known techniques for plant cell transformations, such as by means of liposomes, by electroporation or by vector systems based on plant viruses or pollen, can be used for transforming monocotyledons and dicotyledons with such a gene part.

Furthermore, DNA sequences other than those present naturally in the BTS02617A, BTS02618A, BTS02654B and BTS02652E strains and encoding the BTS02618A protoxin and toxin can be used for transforming plants and bacteria. In this regard, the natural DNA sequence of these genes can be modified by: 1) replacing some codons with others that code either for the same or different, preferably the same, amino acids; 2) deleting or adding some codons; and/or 3) reciprocal recombination as described by Ge et al. (1991); provided that such modifications do not substantially alter the properties, particularly the insecticidal properties, especially anti-lepidoptera properties, of the encoded, insecticidally effective portions of the BTS02618A protoxin (e.g., toxin). For example, an artificial bTS02618A gene or gene part of this invention, as described above, having a modified codon usage, could be used in certain circumstances instead of a natural insecticidally effective bTS02618A gene part in a bTS02618A chimeric gene of this invention for transforming plants.

Also, other DNA recombinants containing all or part of the bTS02618A gene in association with other foreign DNA, particularly the DNA of vectors suitable for transforming plants and microorganisms other than *E. coli*, are encompassed by this invention. In this regard, this invention is not limited to the specific plasmids containing the bTS02618A gene, or parts thereof, that were heretofore described, but rather, this invention encompasses any DNA recombinants containing DNA sequences that are their equivalent. Further, the invention relates to all DNA recombinants that include all or part of the bTS02618A gene and that are suitable for transforming microorganisms (e.g., plant associated bacteria such as other *Bacillus thuringiensis* strains, *Bacillus subtilis*, *Pseudomonas*, and Xanthomonas or yeasts such as *Streptomyces cerevisiae*) under conditions which enable all or part of the gene to be expressed and to be recoverable from said microorganisms or to be transferred to a plant cell.

Example 7

Construction of an Artificial bTS02618A Gene, Encoding the BTS02618A Toxin

Based on the amino acid sequence of the BTS02618A toxin, an artificial DNA sequence encoding substantially the same protein was designed. At first, a DNA sequence for the artificial BTS02618A toxin gene was designed, using corn-preferred codons (Murray et al., 1989). During the design of the artificial gene, TA and CG doublets at codon position 2 and 3 were avoided. The artificial gene was also corrected for local high GC-content (GC stretches of more than 5 bp were avoided). Also, suitable restriction sites were incorporated throughout the gene. So the final gene did not always use the most preferred corn codons. The artificial gene was synthesized on an Applied Biosystems 380B DNA synthesizer using standard cyanoethyl phosphoramidite chemistry. The oligonucleotides were gel purified and assembled into full length fragments using known techniques. See also, the method of Davies et al. (1991). The artificial toxin gene also carried a deletion of codon 2 to codon 43 of the BTS02618A coding sequence, and codon 44 is preceded by an ATG (start) and GCT (Ala) codon, to create a suitable translation initiation context as proposed by Joshi (1987). The C-terminal end of the artificial bTS02618A toxin gene contained some codons in addition to the determined minimal toxic gene fragment, because of the presence of a suitable maize translational stop context in this further C-terminal part.

The chimeric gene construct containing the artificial bTS02618A gene is introduced into corn cells as described above. Most of the corn plants that are regenerated from these cells and that are identified as transformed are insecticidal because of expression of the bTS02618A gene. Northern and Southern analysis of some selected transgenic corn plants show the stable integration of the transgene and the presence of readily detectable levels of BTS02618A mRNA expression. These plants also show good insect control, and the degree of insecticidal activity is linked to the quantity of the Bt protein present in the tissues, as determined by ELISA.

It is believed that any method known for transforming corn so that it expresses the BTS02618A protein at sufficient levels can be used to develop insect-resistant corn. In this regard, it may preferred to express at least 2 non-competitively binding Bt proteins, such as CryIAb and BTS02618A in one plant to prevent the development of insect resistance.

Example 8

Design of a New Variant of the BTS02618A Protein

To prevent further proteolytic cleavage of the BTS02618A about 69 kD toxin, a new variant of the BTS02618A protein was made. In one new variant of this protein, the Arg at amino acid position 123 in SEQ ID. No. 6 was replaced with a Lys (the BTS02618Aa protein). In another variant, the Arg at position 123 in SEQ ID. No. 6 was replaced by Ala (the BTS02618Ab protein). These proteins were found to be more resistant to protease treatment (i.e., the proteins yielded no about 55 kD protein) and insect assays confirmed that their toxicity was retained. The amino acid sequence of the BTS02618Aa toxin is shown in SEQ ID. No. 9.

Other examples having the amino acid sequence changes around the protease cleavage site are made and are also found to have more resistance to protease activity, while retaining their insecticidal activity.

Also, an artificial gene encoding a BTS02618Aa toxin fragment was designed. Besides N- and C-terminal deletions and the addition of a Met and an Ala codon at positions 1 and 2 (as for the DNA of SEQ ID. No. 6), this gene differs in one codon from the synthetic gene of SEQ ID. No. 6: the Arg codon (CGC) was replaced by a Lys (AAG) codon. The other nucleotides were the same as for the artificial bTS02618A gene of SEQ ID. No. 6. Such a modification was made by PCR-mediated mutagenesis, starting from the bTS02618A artificial gene, using the appropriate primers. Essentially, a PCR-generated and restriction enzyme-digested fragment having the mutated codon at position 123 was inserted into the corresponding site of the digested bTS02618A gene of SEQ ID. No. 6 to give the DNA of SEQ ID. No. 8.

Corn plants are also transformed with the bTS02618Aa gene, following the procedures described above. Selected transformed corn plants expressing the bTS02618Aa gene are insecticidal for *Ostrinia nubilalis* larvae. It is believed that any method described in the Detailed Description can be used for expressing the above Bt genes in transformed corn plants, either alone or in combination with other Bt genes. A particularly preferred candidate is a DNA sequence encoding the CryIAb protein. Following routine procedures, appropriate lines having desired qualities can be selected between the to obtained regenerants.

Example 9

Binding of BTS02618A Toxin to Insect Gut Membranes

The BTS02618Aa toxin was found not to inhibit binding of the CryIAb toxin to midgut membrane vesicles of *Ostrinia nubilalis*.

In this experimental setup, the proteins used were: the Lysine mutant of BTS02618A (BTS02618Aa), non-biotinylated; CryIAb, non-biotinylated; and biotinylated (and biologically active) CryIAb. All ICPs used were trypsin resistant toxins. The following combinations were tested:

Biotinylated CryIAb×no competitor;

Biotinylated CryIAb×1000-fold excess of CryIAb toxin;

Biotinylated CryIAb×1000-fold excess of BTS02618Aa toxin.

For these experiments, 10 ng biotinylated CryIAb, with or without an excess of an unlabeled crystal protein, was mixed with 10 microgram brush border membrane vesicles derived from larval midguts of *Ostrinia nubilalis*. These vesicles were prepared according to the method of Wolfersberger et al. (1987). These mixtures were made in PBS (8 mM Na2HPO4, 2 mM KH2PO4, 150 mM NaCl, pH 7.4) containing 0.1% BSA. The mixtures were incubated during 1 hour at room temperature and were then centrifuged for 10 minutes. After washing the pellet in 500 microliter PBS-0.1% BSA, the pellet was centrifuged again and dissolved in sample buffer for SDS-PAGE. The samples were run on a 10% polyacrylamide gel. The gel was blotted at room temperature during two hours on a semi-dry blotting apparatus (LKB Novablot; the blotting buffer used was: 39 mM glycine, 48 mM Tris, 0.0375% (w/v) sodium dodecyl sulphate, 20% methanol). The membrane was blocked for at least 2 hours in TBS (10 mM Tris, 150 mM NaCl, pH 7,6) with 0.1% BSA, followed by incubation with a streptavidin-peroxidase conjugate, diluted 1/1000 in TBS-0.1% BSA for 45 minutes. The membrane was washed for 4 times 5 minutes and once for 15 minutes with TBS- 0.2% Tween 20. Between the wash steps, the blot was thoroughly washed under the tap. The membrane was incubated in ECL reagent (Amersham) for 1 minute and was then exposed to X-ray film.

For the biotinylated CryIAb, a band corresponding to bound toxin was observed on the X-ray film. When biotinylated CryIAb toxin was incubated in the presence of excess CryIAb toxin, no band was observed on the film: as expected, the excess unlabeled toxin had displaced the labeled toxin. For the biotinylated CryIAb toxin in the presence of an excess of the BTS02618Aa toxin, a band corresponding to bound biotinylated CryIAb was seen: unlabeled BTS02618Aa toxin was apparently unable to compete with CryIAb for binding to the vesicles, indicating that BTSO2618Aa binds to another receptor other than CryIAb in *Ostrinia nubilalis*.

In a similar setup, unlabeled CryIAb toxin did not compete for the receptors of biotin-labeled and biologically active BTS02618Aa toxin, while such competition was observed with an excess of unlabeled BTS02618Aa toxin.

Thus, the BTS02618A protein recognizes a different receptor site in Ostrinia midgut membranes, and can be used in a strategy to delay or prevent the development of insect resistance or to combat insects resistant to the CryIAb toxin, e.g., by expressing the CryIAb and the BTS02618A toxin in a plant. Since both toxins are highly active against a group of major insect pests and apparently recognize different receptor molecules, their use in transgenic plants such as corn and vegetables, provides a supplemental advantage. Corn plants can be transformed with the cryIAb and bTS02618Aa gene with any method available in the art, such as crossing plants expressing either toxin, or any of the methods described in EP publication number 408 403.

TABLE 1

Activity of CryI proteins towards several lepidopteran insect pests: + and − indicates the presence or absence of insecticidal activity, +/− indicates low activity (according to Van Frankenhuyzen (1993)), NA indicates no data available, the protein BTS02618A is abbreviated as 2618A (data of Van Frankenhuyzen (1993) and this invention (for *A. ipsilon* and 2618A)).

|   | 2618A | IAb | IAc | IB | IC | IF |
|---|---|---|---|---|---|---|
| S. exiqua | + | +/− | − | − | + | + |
| S. littoralis | + | − | − | − | + | NA |
| H. virescens | + | + | + | − | +/− | + |
| A. ipsilon | + | NA | − | NA | NA | NA |
| O. nubilalis | + | + | + | NA | NA | + |
| P. xylostella | + | + | + | + | + | NA |
| M. brassica | + | + | − | − | + | NA |

TABLE 2

$LC_{50}$–$LC_{95}$ assays with spore-crystal mixtures of recombinant Bt's. Test were performed as described in the text. Values indicate the number of spore-crystals × $10^6$ per square cm of diet agar.

| Strain | $LC_{50}$ | $LC_{95}$ | F195 min-max | Slope |
|---|---|---|---|---|
| Bt kurstaki HD-1 | 8.9 | 91.2 | 3.9–15.4 | 1.6 ± 0.4 |
| HD-1/1 (bTS02618A) | 0.4 | 1.7 | 0.1–0.6 | 2.5 ± 0.7 |
| HD-1/2 (bTS02618A) | 0.4 | 0.93 | 0.2–0.5 | 4.3 ± 1.2 |
| BTS02618A | 1.5 | 4.3 | 0.9–2.1 | 3.6 ± 0.9 |

REFERENCES

Adang et al.(1985). Gene 36, 289.
Bennetzen & Hall.(1982).J. Biol. Chem. 257, 3026–3031.
Berhard, K. and Utz, R., "Production of *Bacillus thuringiensis* insecticides for experimental and commercial uses", In *Bacillus thuringiensis*, An Environmental Biopesticide: Theory and Practice, pp.255–267, eds. Entwistle, P. F., Cory, J. S., Bailey, M. J. and Higgs, S., John Wiley and Sons, New York (1993).
Brizzard & Whiteley (1988). Nucl. Acids Res. 16, 2723–2724.
Callis et al.(1987). Genes and Development 1, 1183–1200.
Chassy, B. M., Mercenier, A. and Flickinger, J., Trends Biotechnol. 6, 303–309 (1988).
Cohen et al., PNAS, 70, 3240–3244 (1973).
D'Halluin et al.(1992).The Plant Cell 4, 1495–1505.
Datta S., Peterhans A., Datta K. and Potrykus I., Bio/Technology 8, 736–740 (1990).
Davies, L. et al. (1991). Society for Applied Bacteriology, Technical Series n 28, pp. 351–359.

Deblaere, R., Bijtebier, B. De Greve, H., Debock, F., Schell, J., Van Montagu, M. and Leemans, J., Nucleic Acids Research 13, 4777–4788 (1985).

Dulmage, H. T., "Production of Bacteria for Biological Control of Insects" in *Biological Control in Crop Production*, Ed. Paparizas, D. C., Osmun Publishers, Totowa, N.J., USA, pp. 129–141 (1981).

Finney, Probit Analysis, 3rd Edition, Cambridge University Press (1971)

Franck, Guilley, Jonard, Richards and Hirth, Cell 21, 285–294 (1980)

French, B. T., Maul, H. N. and Maul, G. G., Anal.Biochem. 156, 417–423 (1986)

Fromm M., Morrish F., Armstrong C., Williams R., Thomas J. and Klein T., Bio/Technology 8, 833–839 (1990).

Gardner, Howarth, Hahn, Brown-Luedi, Shepard and Messing, Nucleic Acids Research 9, 2871–2887 (1981)

Ge A., Rivers D., Milne R. and Dean D., J. Biol. Chem. 266, 17954–17958 (1991)

Gielen, J., De Beukeleer, M., Seurinck, J., Deboeck, F., De Greve, H., Lemmers, M., Van Montagu, M. and Schell, J., EMBO J 3, 835–845 (1984).

Gleave, A. P., Hegdes, R. J. and Broadwell, A. H., J. Gen. Microbiol. 138, 55–62 (1992).

Gordon-Kamm W., Spencer M., Mangano M., Adams T., Daines R., Start W., O'Brien J., Chambers S., Adams W., Willets N., Rice T., Mackey C., Krueger R., Kausch A. and Lemaux P., The Plant Cell 2, 603–618 (1990).

Gould, J., Devey, M., Hasegawa, O., Ulian, E. C., Peterson, G. and Smith, R. H., Plant Physiol. 95, 426–434 (1991).

Ho et al.(1989). Gene 77, 51–59.

Höfte, H., De Greve, H., Seurinck, J., Jansens, S., Mahillon, J., Ampe, Vandekerckhove, J, Vanderbruggen, H., Van Montagu, M., Zabeau, M. and Vaeck, M., Eur. J. Biochem. 161, 273–280 (1986)

Höfte, H., Van Rie, J., Jansens, S., Van Houtven, A., Verbruggen, H. and Vaeck, M., Applied and Environmental Microbiology 54, 2010–2017 (1988)

Höfte H. and Whiteley H. R., Microbiological Review 53, 242–255 (1989).

Hull and Howell, Virology 86, 482–493 (1987)

Itakura et al.(1977). Science 198, 1056–1063.

Joshi, C. P.(1987). Nucl. Acids Res. 16, 6643–6653.

Klein et al.(1992). Bio/Technology 10, 286–291.

Koziel et al.(1993). Bio/Technology 11, 194–200.

Lereclus, D.; Vallade, M. ; Chaufaux, J.; Arantes, O. & Rambaud, S., Bio/Technology 10, 418 (1992).

MacIntosh, S. C. et al, J. Invertebrate Patholog. 56, 258–266 (1990).

Mahillon, J. and Delcour, J., J. Microbiol. Methods 3, 69–73 (1984).

Mahillon, J. and Seurinck, J., Nucl. Acids Res. 16, 11827–11828 (1988).

Mahillon et al, Plasmid 19, 169–173 (1988).

Mahillon et al, FEMS Microbiol. Letters 60, 205–210 (1989).

Maas et al.(1991). Plant Mol. Biol. 16, 199–207.

Maxam, A. M. and Gilbert, W., Methods in Enzymol. 65, 499–560 (1980).

Mogen et al., *The Plant Cell,* 2, 1261–1272 (1990).

Murray, E., Lotzer, J. and Eberle, M., Nucleic Acids Research 17(2), 477–498 (1989).

Omirulleh et al.(1993). Plant Mol. Biol. 21, 415–428.

Rupar et al., *Applied & Environ. Micro.,* 57 3337–3344 (1991)

Schnepf et al. (1985). Journal of Biological Chemistry 260, 6264.

Shimamoto K., Terada R., Izawa T. and Fujimoto H., Nature 338, 274–276 (1989).

Smulevitch, S. V., Osterman, A. L., Shevelev, A. B., Kaluger, S. V., Karasin, A. I., Kadyrov, R. M., Zagnitko, O. P., Chestukhina, G. G. and Stepanov, V. M., FEBS Lett. 293, 1(2), 25–28 (1991).

Spencer et al.(1992). Plant Mol. Biol. 18, 201–210.

Stanssens P., Opsomer C., McKeown Y., Kramer W., Zabeau M. and Fritz H. J., Nucleic Acids Research 12, 4441–4454 (1989).

Vaeck, M., Reynaerts, A., Höfte, H., Jansens, S., De Beuckeleer, M., Dean, C., Zabeau, M., Van Montagu, M. and Leemans, J., Nature 327, 33–37(1987).

Van Frankenhuyzen, "The Challenge of Bacillus thuringiensis", in "*Bacillus thuringiensis*, An Environmental Biopesticide: Theory and Practice", pp.1–35, eds. Entwistle, P. F., Cory, J. S., Bailey, M. J. and Higgs, S., John Wiley and Sons, New York (1993).

Velten, J., Velten, L., Hain, R. and Schell, J., EMBO J 3, 2723–2730 (1984).

Velten, J. and Schell, J. Nucleic Acids Research 13, 6981–6998 (1985)

Visser, B., Bosch, D. and Honee, G., "Domain-Structure Studies of *Bacillus thuringiensis* Crystal Proteins: A Genetic Approach", In *Bacillus thuringiensis*, An Environmental Biopesticide: Theory and Practice, pp.71–88, eds. Entwistle, P. F., Cory, J. S., Bailey, M. J. and Higgs, S., John Wiley and Sons, New York (1993).

Wada et al. (1990). Nucl. Acids Res. 18, 2367–1411.

Walters et al.(1992). Plant Mol. Biol. 18, 189–200.

White et al.(1989). Trends in Genet. 5, 185–189.

Wolfersberger, M., Luthy, P., Maurer, A., Parenti, P., Sacchi, V. F., Giordana, B. and Hanozet, G. M. (1987) Comp. Biochem. Physiol. 86A, 301–308.

Wu et al.(1991). *The Plant Journal,* 4, 535–544 (1993).

Yannisch-Perron, C., Vierra, J. and Messing, J., Gene 33, 103–119 (1985).

---

What is claimed is:

1. A process for controlling a Lepidopteran insect pest, said process comprising: contacting said insect pest with a protein comprising the amino acid sequence of SEQ ID NO. 5 from amino acid position 44 to amino acid position 658, wherein the Arginine at amino acid position 164 in SEQ ID No. 5 is replaced by another amino acid.

2. The process of claim 1, wherein said Arginine at amino acid position 164 in SEQ ID No. 5 is replaced with a Lysine or an Alanine.

3. The process of claim 1, wherein said protein comprises the amino acid sequence of SEQ ID No. 9.

4. The process according to any one of claims 1 to 3, wherein said Lepidopteran insect is selected from the group consisting of: *Agrotis epsilon, Agrotis segetum, Spodoptera exigua, Spodoptera littoralis, Spodoptera frugiperda, Mamestra brassica, Heliothis virescens, Ostrinia nubilalis, Phthorimaea operculella* and *Plutella xylostella.*

5. A process for controlling *Agrotis segetum* or *Phthorimaea operculella* comprising: contacting *Agrotis segetum* or *Phthorimaea operculella* with a protein which is selected form the group consisting of: a protein comprising the amino acid sequence of SEQ ID No. 5 from amino acid position 44 to amino acid position 658; a protein comprising the amino acid sequence of SEQ ID No. 5 from amino acid position 44 to amino acid position 658 wherein the amino acid at position 164 in SEQ ID No. 5 is a Lysine or an Alanine; and a protein comprising the amino acid sequence of SEQ ID No. 9.

* * * * *